United States Patent [19]

Zondler et al.

[11] Patent Number: 4,980,355
[45] Date of Patent: Dec. 25, 1990

[54] COMPOSITIONS FOR PROTECTING PLANTS AGAINST DISEASE

[75] Inventors: Helmut Zondler, Bottmingen; Alfred Meyer, Basel, both of Switzerland; Wolfgang Eckhardt, Lörrach, Fed. Rep. of Germany; Walter Kunz, Oberwil, Switzerland

[73] Assignee: Ciba-Geigy Corporation, Ardsley, N.Y.

[21] Appl. No.: 319,017

[22] Filed: Mar. 3, 1989

[30] Foreign Application Priority Data

Mar. 9, 1988 [CH] Switzerland .............. 887/88

[51] Int. Cl.$^5$ ............ A01N 43/54; A01N 43/58; A01N 43/40; A01N 43/60; C07D 401/12; C07D 401/14

[52] U.S. Cl. .................. 514/256; 514/252; 514/255; 514/269; 514/272; 514/274; 514/275; 514/316; 514/318; 514/332; 514/333; 514/335; 514/232.2; 514/235.8; 514/236.5; 514/235.5; 546/187; 546/193; 546/194; 546/262; 546/256; 546/261; 544/114; 544/120; 544/122; 544/123; 544/129; 544/130; 544/131; 544/124; 544/82; 544/238; 544/300; 544/310; 544/316; 544/317; 544/319; 544/320; 544/321; 544/327; 544/328; 544/331; 544/324; 544/322; 544/405

[58] Field of Search ............ 544/114, 120, 122, 123, 544/129, 130, 131, 124, 82, 238, 300, 310, 316, 317, 319, 320, 321, 327, 328, 331, 324, 322, 405; 546/187, 193, 194, 262, 256, 261; 514/252, 255, 256, 269, 272, 274, 275, 316, 318, 332, 333, 335, 232.2, 235.8, 236.5, 235.5

[56] References Cited

U.S. PATENT DOCUMENTS 4,137,067 1/1979 Gätzi .......................... 71/94

FOREIGN PATENT DOCUMENTS 1072443 2/1980 Canada .
384929 2/1965 Switzerland .
923387 4/1963 United Kingdom .

OTHER PUBLICATIONS

Klosa., Chemical Abstracts, vol. 64, entry 9706(d), 1966.
LeDouarec et al., Chemical Abstracts, vol. 65, entry 2258(a), 1966.
Chem. Abstract, 57: 4769a, (1962), abstract of Acta Fa. Pharm. Brun. Bratislar., 4, 65, 66, (1962).

Primary Examiner—John M. Ford
Attorney, Agent, or Firm—George R. Dohmann; Edward McC. Roberts

[57] ABSTRACT

Novel substituted isonicotinic acid amides of the general formula

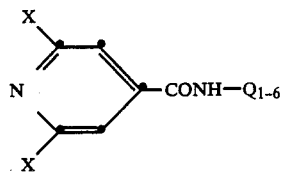

in which
X in ortho/ortho'-position are equal and represent fluorine, chlorine, bromine or iodine;
$Q_1$ is unsubstituted pyridimin-4-yl, or pyrimidin-4-yl substituted by $R_1$, $R_2$ and $R_3$;
$Q_2$ is unsubstituted pyrimidin-2-yl, or pyrimidin-2-yl substituted by $R_1$, $R_2$ and $R_3$;
$Q_3$ is unsubstituted pyrimidin-5-yl, or pyrimidin-5-yl substituted by $R_1$, $R_2$ and $R_3$;
$Q_4$ is pyridin-2-yl, pyridin-3-yl or pyridin-4-yl each of which is unsubstituted or substituted by $R_1$, $R_2$ and $R_3$;
$Q_5$ is pyridazin-3-yl or pyridazin-4-yl each of which is unsubstituted or substituted by $R_1$, $R_2$ and $R_3$;
$Q_6$ is unsubstituted pyrazin-2-yl, or pyrazin-2-yl substituted by $R_1$, $R_2$ and $R_3$;
$R_1$, $R_2$, $R_3$ are hydrogen, halogen, $C_1$–$C_6$alkyl, $C_1$–$C_6$haloalkyl having from 1 to 3 halogen atoms, $C_1$–$C_6$alkoxy, $C_2$–$C_6$alkoxyalkyl, $C_1$–$C_6$thioalkyl, $C_1$–$C_6$haloalkoxy having from 1 to 5 halogen atoms, $C_3$–$C_6$alkenyloxy, $C_3$–$C_6$alkynyloxy, $C_3$–$C_6$thioalkenyl, $C_3$–$C_6$cycloalkyl, $C_3$–$C_6$cycloalkyl substituted by methyl, or nitro, cyano, the radical $CH(OR_4)_2$ or $COOR_4$ in which $R_4$ is $C_1$–$C_4$alkyl; also phenyl, phenoxy, thiophenyl, benzyl, benzyloxy or thiobenzyl; or phenyl, phenoxy, thiophenyl, benzyl, benzyloxy or thiobenzyl each substituted at least once by $C_1$–$C_3$alkyl, $C_1$–$C_3$-alkoxy, $C_1$–$C_3$haloalkyl having from 1 to 3 halogen atoms, halogen, nitro or by cyano; and also $N(R_5)R_6$ in which $R_5$ and $R_6$, independently of one another, are each $C_1$–$C_6$alkyl; and furthermore piperidinyl, pyrrolidinyl, morpholinyl, imidazolyl or triazolyl, or piperidinyl, pyrrolidinyl, morpholinyl, imidazolyl or triazolyl each substituted by $C_1$–$C_3$alkyl, $C_1$–$C_3$alkoxy, $C_1$–$C_3$haloalkyl having from 1 to 3 halogen atoms, halogen, nitro or by cyano.

The novel active ingredients have plant-protecting properties and are suitable especially for the preventive protection of plants against attack by phytopathogenic microorganisms such as fungi, bacteria and viruses.

6 Claims, No Drawings

COMPOSITIONS FOR PROTECTING PLANTS AGAINST DISEASE

The present invention relates to novel isonicotinic acid amides substituted by heterocycles of the following formula I. The invention relates also to the preparation of those substances and to compositions containing at least one of those compounds as active ingredient. The invention furthermore relates to the preparation of the said compositions and to the use of the active ingredients or compositions for protecting plants against attack by harmful microorganisms, for example plant-damaging fungi, bacteria and viruses.

The compounds of the invention correspond to the general formula I

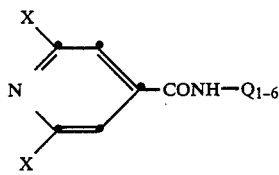

(I)

in which
- X in ortho/ortho'-position are equal and represent fluorine, chlorine, bromine or iodine, preferably fluorine, chlorine or bromine and especially preferred chlorine;
- $Q_1$ is unsubstituted pyrimidin-4-yl, or pyrimidin-4-yl substituted by $R_1$, $R_2$ and $R_3$;
- $Q_2$ is unsubstituted pyrimidin-2-yl, or pyrimidin-2-yl substituted by $R_1$, $R_2$ and $R_3$;
- $Q_3$ is unsubstituted pyrimidin-5-yl, or pyrimidin-5-yl substituted by $R_1$, $R_2$ and $R_3$;
- $Q_4$ is pyridin-2-yl, pyridin-3-yl or pyridin-4-yl each of which is unsubstituted or substituted by $R_1$, $R_2$ and $R_3$;
- $Q_5$ is pyridazin-3-yl or pyridazin-4-yl each of which is unsubstituted or substituted by $R_1$, $R_2$ and $R_3$;
- $Q_6$ is unsubstituted pyrazin-2-yl, or pyrazin-2-yl substituted by $R_1$, $R_2$ and $R_3$;
- $R_1$, $R_2$, $R_3$ are hydrogen, halogen, $C_1$-$C_6$alkyl, $C_1$-$C_6$haloalkyl having from 1 to 3 halogen atoms, $C_1$-$C_6$alkoxy, $C_2$-$C_6$alkoxyalkyl, $C_1$-$C_6$thioalkyl, $C_1$-$C_6$haloalkoxy having from 1 to 5 halogen atoms, $C_3$-$C_6$alkenyloxy, $C_3$-$C_6$alkynyloxy, $C_1$-$C_6$thioalkenyl, $C_3$-$C_6$cycloalkyl, $C_1$-$C_6$cycloalkyl substituted by methyl, or nitro, cyano, the radical $CH(OR_4)_2$ or $COOR_4$ in which $R_4$ is $C_2$-$C_4$alkyl; $R_1$, $R_2$, $R_3$ are also phenyl, phenoxy, thiophenyl, benzyl, benzyloxy or thiobenzyl; or phenyl, phenoxy, thiophenyl, benzyl, benzyloxy or thiobenzyl each substituted at least once by $C_1$-$C_3$alkyl, $C_1$-$C_3$alkoxy, $C_1$-$C_3$haloalkyl having from 1 to 3 halogen atoms, halogen, nitro or by cyano; and $R_1$, $R_2$, $R_3$ are also $N(R_5)R_6$ in which $R_5$ and $R_6$, independently of one another, are each $C_1$-$C_6$alkyl; and furthermore piperidinyl, pyrrolidinyl, morpholinyl, imidazolyl or triazolyl, or piperidinyl, pyrrolidinyl, morpholinyl, imidazolyl or triazolyl each substituted by $C_1$-$C_3$alkyl, $C_1$-$C_3$alkoxy, $C_1\propto C_3$haloalkyl having from 1 to 3 halogen atoms, halogen, nitro or by cyano.

Alkyl on its own or as a component of another substituent is to be understood as meaning straight-chain or branched alkyl. Depending on the number of carbon atoms indicated it represents, for example, one of the following groups: methyl, ethyl and the isomers of propyl, butyl, pentyl or hexyl, such as, for example, isopropyl, isobutyl, tert.-butyl, sec.-butyl or isopentyl.

Alkenyl is, for example, propenyl-(1), allyl, butenyl-(1), butenyl-(2) or butenyl-(3) and alkynyl is, for example, propynyl-(2), butynyl-(1) or pentynyl-(4).

a narrower scope of the invention is represented by formula I in which X in ortho/ortho'-position are equal and represent fluorine, chlorine, bromine or iodine;
- $Q_1$ is unsubstituted pyrimidin-4-yl, or pyrimidin-4-yl substituted by $R_1$, $R_2$ and $R_3$;
- $Q_2$, is unsubstituted pyrimidin-2-yl, or pyrimidin-2-yl substituted by $R_1$, $R_2$ and $R_3$;
- $Q_3$ is unsubstituted pyrimidin-5-yl, or pyrimidin-5-yl substituted by $R_1$, $R_2$ and $R_3$;
- $Q_4$ is pyridin-2-yl, pyridin-3-yl or pyridin-4-yl each of which is unsubstituted or substituted by $R_1$, $R_1$ and $R_3$;
- $Q_5$ is pyridazin-3-yl or pyridazin-4-yl each of which is unsubstituted or substituted by $R_1$, $R_2$ and $R_3$;
- $Q_6$ is unsubstituted pyrazin-2-yl, or pyrazin-2-yl substituted by $R_1$, $R_2$ and $R_3$;
- $R_1$, $R_2$, $R_3$ are hydrogen, halogen, $C_1$-$C_6$alkyl, $C_1$-$C_6$haloalkyl having from 1 to 3 halogen atoms, $C_1$-$C_6$alkoxy, $C_1$-$C_6$alkoxyalkyl, $C_1$-$C_6$thioalkyl, $C_1$-$C_6$haloalkoxy having from 1 to 5 halogen atoms, $C_1$-$C_6$alkenyloxy, $C_3$-$C_6$alkynyloxy, $C_3$-$C_6$thioalkenyl, $C_3$-$C_6$cycloalkyl, nitro, cyano or $COOR_4$ in which $R_4$ is $C_1$-$C_4$alkyl; $R_1$, $R_1$, $R_1$ are also phenyl, phenoxy, thiophenyl, benzyl, benzyloxy or thiobenzyl; or phenyl, phenoxy, thiophenyl, benzyl, benzyloxy or thiobenzyl each substituted at least once by $C_1$-$C_3$alkyl, $C_1$-$C_3$alkoxy, $C_1$-$C_3$haloalkyl having from 1 to 3 halogen atoms, halogen, nitro or by cyano; and also $N(R_5)R_6$ in which $R_5$ and $R_6$, independently of one another, are each $C_1$-$C_6$alkyl; and furthermore $R_1$, $R_2$, $R_1$ are piperidinyl, pyrrolidinyl, morpholinyl, imidazolyl or triazolyl, or piperidinyl, pyrrolidinyl, morpholinyl, imidazolyl or triazolyl each substituted by $C_1$-$C_3$alkyl, $C_1$-$C_3$alkoxy, $C_1C_3$haloalkyl having from 1 to 3 halogen atoms, halogen, nitro or by cyano.

The compounds of formula I can be divided into the following groups on the basis of their particular plant-protecting properties:
- (A) Compounds in which $Q_1$ is pyrimidin-4-yl substituted by $R_1$, $R_2$ and $R_3$, and X, $R_1$, $R_2$ and $R_3$ are as defined for formula I;
- (B) Compounds in which $Q_2$ is pyrimidin-2-yl substituted by $R_1$, $R_2$ and $R_3$, and X, $R_1$, $R_2$ and $R_3$ are as defined for formula I;
- (C) Compounds in which $Q_1$ is pyrimidin-5-yl substituted by $R_1$, $R_2$ and $R_3$, and X, $R_1$, $R_2$ and $R_3$ are as defined for formula I;
- (D) Compounds in which $Q_4$ is pyridin-2-yl, pyridin-3-yl or pyridin-4-yl each substituted by $R_1$, $R_2$ and $R_3$, and X, $R_1$, $R_2$ and $R_3$ are as defined for formula I;
- (E) Compounds in which $Q_5$ is pyridazin-3-yl or pyridazin-4-yl each substituted by $R_1$, $R_2$ and $R_3$, and X, $R_1$, $R_2$ and $R_3$ are as defined for formula I;
- (F) Compounds in which $Q_5$ is pyrazin-2-yl substituted by $R_1$, $R_2$ and $R_3$, and X, $R_1$, $R_1$ and $R_1$ are as defined for formula I.

Of the above-mentioned groups of compounds the following sub-groups of compounds of formula I are preferred on account of their outstanding biological activity:

(A₁) Compounds in which X in ortho/ortho'-position are equal and represent fluorine, chlorine, bromine or iodine, $Q_1$ is pyrimidin-4-yl and $R_1$, $R_2$ and $R_3$ as substituents in the 2-, 5- and 6-positions are hydrogen, halogen, $C_1$–$C_6$alkyl, $C_1$–$C_3$-haloalkyl having from 1 to 3 halogen atoms, $C_1$–$C_4$alkoxy, $C_2$≃$C_4$alkoxyalkyl, $C_1$–$C_4$thioalkyl, $C_1$–$C_4$haloalkoxy having from 1 to 3 halogen atoms, $C_3$–$C_4$alkenyloxy, $C_3$–$C_4$alkynyloxy, $C_3$–$C_4$thioalkenyl, $C_1$–$C_5$cycloalkyl, nitro, cyano or $COOR_4$ in which $R_4$ is $C_1$–$C_4$-alkyl, and also phenyl, phenoxy, thiophenyl or benzyl, or phenyl or phenoxy each substituted by from 1 to 3 halogen atoms; and furthermore $N(R_5)R_6$ in which $R_5$ and $R_6$, independently of one another, are each $C_1$–$C_4$alkyl; as well as piperidinyl, pyrrolidinyl, morpholinyl, imidazolyl or triazolyl, or piperidinyl, pyrrolidinyl, morpholinyl, imidazolyl or triazolyl each substituted by $C_1$–$C_3$alkyl or by halogen.

(A₂) Compounds in which X in ortho/ortho'-position are equal and represent fluorine, chlorine or bromine, $Q_1$ is pyrimidin-4-yl and $R_1$, $R_2$ and $R_3$ in the 2-, 5- and 6-positions are hydrogen, fluorine, chlorine, bromine, $C_1$–$C_4$alkyl, $C_1$–$C_2$haloalkyl having from 1 to 3 fluorine or chlorine atoms, $C_1$–$C_3$alkoxy, $C_2$–$C_4$alkoxyalkyl, $C_1$–$C_4$thioalkyl, $C_2$–$C_2$haloalkoxy having from 1 to 3 fluorine or chlorine atoms, $C_3$–$C_4$alkenyloxy, $C_3$–$C_4$alkynyloxy, cyclopropyl, nitro, cyano or $COOR_4$ in which $R_4$ is $C_1$–$C_4$alkyl; and also phenyl, phenoxy, thiophenyl, benzyl, dimethylamino.

(A₃) Compounds in which X is chlorine, $Q_1$ is pyrimidin-4-yl and $R_1$, $R_2$ and $R_3$ in the 2-, 5- and 6-positions are hydrogen, fluorine, chlorine, bromine, $C_1$–$C_4$alkyl, $C_1$–$C_2$haloalkyl having from 1 to 3 fluorine or chlorine atoms, $C_1$–$C_3$alkoxy, $C_2$–$C_4$alkoxyalkyl, $C_1$–$C_4$thioalkyl, $C_1C_2$-haloalkoxy having from 1 to 3 fluorine or chlorine atoms, $C_3$–$C_4$alkenyloxy, $C_3$–$C_4$alkynyloxy, cyclopropyl, nitro, cyano or $COOR_4$ in which $R_4$ is $C_1$–$C_4$alkyl; and also phenyl, phenoxy, thiophenyl, benzyl, dimethylamino.

(B₁) Compounds in which X in ortho/ortho'-position are equal and represent fluorine, chlorine, bromine or iodine, $Q_2$ is pyrimidin-2-yl and $R_1$, $R_2$ and $R_3$ in the 4-, 5- and 6-positions are hydrogen, halogen, $C_1$–$C_4$alkyl, $C_2$–$C_2$haloalkyl having from 1 to 3 halogen atoms, $C_1$–$C_3$alkoxy, $C_1$–$C_4$thioalkyl, $C_1$–$C_2$haloalkoxy having from 1 to 3 halogen atoms, $C_1$–$C_4$alkenyloxy, $C_3$–$C_4$alkynyloxy, $C_3$–$C_5$cycloalkyl, nitro, cyano or $COOR_4$ in which $R_4$ is $C_1$–$C_4$alkyl; and also phenoxy, thiophenyl, thiobenzyl; and furthermore $N(R_5)R_6$ in which $R_5$ and $R_6$ independently of one another are each $C_1$–$C_2$-alkyl; as well as piperidinyl or morpholinyl, or morpholinyl substituted by $C_1$–$C_3$alkyl or by chlorine.

(B₂) Compounds in which X in ortho/ortho'-position are equal and represent fluorine, chlorine or bromine, $Q_1$ is pyrimidin-2-yl and $R_1$, $R_2$ and $R_3$ in the 4-, 5- and 6-positions are hydrogen, fluorine, chlorine, bromine, $C_1$–$C_4$alkyl, $C_1$–$C_2$haloalkyl having from 1 to 3 fluorine or chlorine atoms, $C_1$–$C_3$alkoxy, $C_2$–$C_4$alkoxyalkyl, $C_1$–$C_4$thioalkyl, $C_1$–$C_2$-haloalkoxy having from 1 to 3 fluorine or chlorine atoms, $C_3$–$C_4$alkenyloxy, $C_1$–$C_4$alkynloxy, cyclopropyl, nitro, cyano or $COOR_4$ in which $R_4$ $C_1$–$C_4$alkyl; and also phenyl, phenoxy, thiophenyl, benzyl, dimethylamino.

(B₃) Compounds in which X is chlorine, $Q_2$ is pyrimidin-2-yl and $R_1$, $R_2$ and $R_3$ in the 4-, 5- and 6-positions are hydrogen, fluorine, chlorine, bromine, $C_1$–$C_4$alkyl, $C_1$–$C_2$haloalkyl having from 1 to 3 fluorine or chlorine atoms, $C_1$–$C_3$alkoxy, $C_2$–$C_4$alkoxyalkyl, $C_1$–$C_4$thioalkyl, $C_1$–$C_2$haloalkoxy having from 1 to 3 fluorine or chlorine atoms, $C_3$–$C_4$alkenyloxy, $C_3$–$C_4$alkynyloxy, cyclopropyl, nitro, cyano or $COOR_4$ in which $R_4$ is $C_1$–$C_4$alkyl; and also phenyl, phenoxy, thiophenyl, benzyl, dimethylamino.

(C₁) Compounds in which X in ortho/ortho'-position are equal and represent fluorine, chlorine, bromine or iodine, $Q_3$ is pyrimidin-5-yl and $R_1$, $R_2$ and $R_3$ are hydrogen, halogen, $C_1$–$C_4$ alkyl, $C_1$–$C_2$haloalkyl having from 1 to 3 halogen atoms, $C_1$–$C_5$alkoxy, $C_2$–$C_4$alkoxyalkenyl, $C_1$–$C_4$thioalkyl, $C_1$–$C_3$haloalkoxy having from 1 to 4 halogen atoms, $C_1$–$C_4$alkenyloxy, $C_1$–$C_4$alkynyloxy, $C_3$–$C_5$cycloalkyl; or phenoxy, thiophenyl or benzyloxy each unsubstituted or substituted by halogen; and furthermore $N(R_5)R_5$ in which $R_5$ and $R_5$, independently of one another, are each $C_1$–$C_2$alkyl; as well as pyrrolidinyl or morpholinyl.

(C₂) Compounds in which X in ortho/ortho'-position are equal and represent fluorine, chlorine or bromine, $Q_1$ is pyrimidin-5-yl and $R_1$, $R_2$ and $R_1$ in the 2-, 4- and 6-positions are hydrogen, fluorine, chlorine, bromine, $C_1$–$C_4$alkyl, $C_1$–$C_2$haloalkyl having from 1 to 3 fluorine or chlorine atoms, $C_1$–$C_3$alkoxy, $C_2$–$C_4$alkoxyalkyl, $C_1$–$C_4$thioalkyl, $C_1$–$C_2$haloalkoxy having from 1 to 3 fluorine or chlorine atoms, $C_3$–$C_4$alkenyloxy, $C_3$–$C_4$alkynyloxy, cyclopropyl, nitro, cyano or $COOR_4$ in which $R_4$ is $C_1$–$C_4$alkyl; and also phenyl, phenoxy, thiophenyl, benzyl, dimethylamino.

(C₃) Compounds in which X is chlorine, $Q_1$ is pyrimidin-5-yl and $R_1$, $R_2$ and $R_3$ in the 2-, 4- and 6-positions are hydrogen, fluorine, chlorine, bromine, $C_1$–$C_4$alkyl, $C_1$–$C_2$haloalkyl having from 1 to 3 fluorine or chlorine atoms, $C_1$–$C_3$alkoxy, $C_2$–$C_4$alkoxyalkyl, $C_2$–$C_4$thioalkyl, $C_1$–$C_2$haloalkoxy having from 1 to 3 fluorine or chlorine atoms, $C_3$–$C_4$alkenyloxy, $C_3$–$C_4$alkynyloxy, cyclopropyl, nitro, cyano or $COOR_4$ in which $R_4$ is $C_1$–$C_4$alkyl; and also phenyl, phenoxy, thiophenyl, benzyl, dimethylamino.

(D₁) Compounds in which X in ortho/ortho'-position are equal and represent fluorine, chlorine, bromine or iodine, $Q_4$ is pyridin-2-yl and $R_1$, $R_2$ and $R_1$ in the 3-, 4-, 5- and 6-positions are hydrogen, halogen, $NO_2$, $C_1$–$C_4$-alkyl, $C_1$–$C_4$-haloalkyl having from 1 to 3 halogen atoms, $C_1$–$C_3$ alkoxy or $C_1$–$C_4$thioalkyl.

(D₂) Compounds in which X in ortho/ortho'-position are equal and represent fluorine, chlorine, bromine or iodine, Q. is pyridin-3-yl and $R_1$, $R_2$ and $R_3$ in the 2-, 4-, 5- and 6-positions are hydrogen, halogen, $NO_2$, $C_1$–$C_4$-alkyl, $C_1$–$C_2$haloalkyl having from 1 to 3 halogen atoms, $C_1$–$C_4$alkoxy or $C_1$–$C_4$thioalkyl.

(D₃) Compounds in which X in ortho/ortho'-position are equal and represent fluorine, chlorine, bromine or iodine, $Q_4$ is pyridin-4-yl and $R_1$, $R_2$ and $R_3$ in the 2-, 3-, 5- and 6-positions are hydrogen, halogen, $NO_2$, $C_1$–$C_4$-alkyl, $C_1$–$C_2$haloalkyl having from 1 to 3 halogen atoms, $C_1$–$C_4$alkoxy or $C_1$–$C_4$thioalkyl.

(E₁) Compounds in which X in ortho/ortho'-position are equal and represent fluorine, chlorine, bromine or iodine, $Q_5$ is pyridazin-3-yl and $R_1$, $R_2$ and $R_3$ in the 4-, 5- and 6-positions are hydrogen, halogen, $C_1$–$C_4$alkyl, $C_1$–$C_4$alkoxy, $C_1$–$C_4$thioalkyl, $C_1$–$C_2$haloalkyl having from 1 to 3 halogen atoms.

($E_2$) Compounds in which X in ortho/ortho'-position are equal and represent fluorine, chlorine, bromine or iodine, $Q_5$ is pyridazin-4-yl and $R_1$, $R_2$ and $R_1$ in the 3-, 5- and 6-positions are hydrogen, halogen, $C_1$–$C_4$alkyl, $C_1$–$C_4$alkoxy, or $C_1$–$C_2$haloalkyl having from 1 to 3 halogen atoms.

($F_1$) Compounds in which X in ortho/ortho'-position are equal and represent fluorine, chlorine, bromine or iodine, $Q_5$ is pyrazin-2-yl and $R_1$, $R_2$ and $R_3$ in the 3-, 5- and 6-positions are hydrogen, halogen, $C_1$–$C_4$alkyl, $C_1$–$C_4$alkoxy, or $C_1$–$C_2$haloalkyl having from 1 to 3 halogen atoms.

The following compounds are distinguished by especially advantageous plant-protecting properties:

N-(2-cyclopropyl-5-ethyl-6-chloropyrimidin-4-yl)-2,6-dichloroisonicotinic acid amide;
N-(2-cyclopropyl-5-methyl-6-chloropyrimidin-4-yl)-2,6-dichloroisonicotinic acid amide;
N-(2,5-dimethyl-6-chloropyrimidin-4-yl)-2,6-dichloroisonicotinic acid amide;
N-(2,5-diethyl-6-chloropyrimidin-4-yl)-2,6-dichloroisonicotinic acid amide;
N-(2-chloro-6-thiomethylpyrimidin-4-yl)-2,6-dichloroisonicotinic acid amide;
N-(2-methoxy-5-chloropyrimidin-4-yl)-2,6-dichloroisonicotinic acid amide;
N-(2,5-dichloropyrimidin-4-yl)-2,6-dichloroisonicotinic acid amide;
N-(2,6-dimethylpyrimidin-4-yl)-2,6-dichloroisonicotinic acid amide;
N-(5-methyl-6-chloropyrimidin-4-yl)-2,6-dichloroisonicotinic acid amide;
N-(5-n-propyl-6-chloropyrimidin-4-yl)-2,6-dichloroisonicotinic acid amide;
N-(5-ethyl-6-chloropyrimidin-4-yl)-2,6-dichloroisonicotinic acid amide;
N-(2,5,6-trichloropyrimidin-4-yl)-2,6-dichloroisonicotinic acid amide;
N-(2-dimethylamino-6-methoxypyrimidin-4-yl)-2,6-dichloroisonicotinic acid amide;
N-(2-ethyl-5-methyl-6-chloropyrimidin-4-yl)-2,6-dichloroisonicotinic acid amide;
N-(2-trifluoroethoxy-5-chloropyrimidin-4-yl)-2,6-dichloroisonicotinic acid amide;
N-(2-methoxy-5-fluoropyrimidin-4-yl)-2,6-dichloroisonicotinic acid amide;
N-(2-chloro-5-fluoropyrimidin-4-yl)-2,6-dichloroisonicotinic acid amide;
N-(2-isopropoxy-5-chloropyrimidin-4-yl)-2,6-dichloroisonicotinic acid amide;
N-(2-isopropyl-6-chloropyrimidin-4-yl)-2,6-dichloroisonicotinic acid amide;
N-(2-chloro-6-n-propylpyrimidin-4-yl)-2,6-dichloroisonicotinic acid amide;
N-(2-n-propoxy-5-chloropyrimidin-4-yl)-2,6-dichloroisonicotinic acid amide;
N-(2-isopropyl-6-ethylthiopyrimidin-4-yl)-2,6-dichloroisonicotinic acid amide;
N-(2-isopropyl-6-isopropylthiopyrimidin-4-yl)-2,6-dichloroisonicotinic acid amide;
N-(2-chloro-6-methylpyrimidin-4-yl)-2,6-dichloroisonicotinic acid amide;
N-pyridin-2-yl-2,6-dichloroisonicotinic acid amide;
N-(6-methylpyridin-2-yl)-2,6-dichloroisonicotinic acid amide;
N-(4-methylpyridin-2-yl)-2,6-dichloroisonicotinic acid amide;
N-(5-chloropyridin-2-yl)-2,6-dichloroisonicotinic acid amide;
N-pyridin-4-yl-2,6-dichloroisonicotinic acid amide.

Some 2,6-dihaloisonicotinic acid derivatives are already known. For example, 2,6-dihaloisonicotinic acid derivatives, such as aliphatic amides, are described as herbicides in British Patent Specification No. 923 387. Furthermore, U.S. Pat. No. 4,137,067 and Canadian Patent Specification No. 1 072 443 disclose 2,6-dichloroisonicotinic acid hydrazides for controlling phytopathogenic microorganisms. In addition, 2,6-dihaloisonicotinic acid derivatives are known as tuberculostatic agents (cf. Acta Fac. Pharm. Brun. Bratislav. 4, 65–66 [1962]; Chem. Abstr. Vol. 57, 1962, 4769b).

It has now surprisingly been found that the use of compounds of formula I of the invention prevents plants from being attacked by harmful microorganisms and thus guards against damage to plants caused by such attack. A characteristic of the active ingredients of the invention is that the protection of the plants can stem both from the direct action on the plant-damaging microorganisms by means of foliar application (direct action) or soil application (systemic action) and from the activation and stimulation of the plant's own defence system (immunisation). The great advantage of the compounds of formula I is that it is possible to ensure the continued health of plants treated with these substances also through their own resources without using microbicidal substances during the vegetation period. Consequently it is possible by using the active ingredients of the invention to avoid the adverse side effects that may occur, for example, with direct parasite control using chemical substances, for example on the one hand as a result of damage to the useful plants (phytotoxicity) and on the other hand as a result of causing the harmful microorganisms to develop a resistance; consequently growth of the useful plants is advantageously completely undisturbed. Owing to the double action of the compounds of formula I of the invention, that is to say on the one hand the direct control of the plant pathogens and on the other hand the increase in the general capacity of plants treated with these active ingredients to defend themselves against pests as a result of immunisation, it is possible to achieve a broadly based protection of plants against disease. The use of the active ingredients of the invention is therefore especially suitable for practical application.

Furthermore, the systemic activity peculiar to the compounds of formula I results in the protective effect being extended also to growing parts of the treated plants.

The general plant-protecting activity of the active ingredients of the invention is effective, for example, against the phytopathogenic fungi belonging to the following classes: Fungi imperfecti (for example Botrytis, Helminthosporium, Fusarium, Septoria, Cercospora and Alternaria); Basidiomycetes (for example of the genera Hemileia, Rhizocotonia, Puccinia); Ascomycetes (for example Venturia, Podosphaera, Erysiphe, Monilinia, Uncinula).

In addition, the active ingredients can be used with particular advantage against the following harmful organisms: fungi, such as, for example, Oomycetes (for example *Plasmopara viticola, Phytophthora infestans, peronospora tabacina,* Pseudoperonospora), Fungi imperfecti (for example *Colletotrichum lagenarium, Piricu-*

*laria oryzae, Cercospora nicotinae*), Ascomycetes (for example *Venturia inaequalis*); bacteria, such as, for example, Pseudomonads (Pseudomonas lachrymans, Pseudomonas tomato, Pseudomonas tabaci); Xanthomonads (for example *Xanthomonas oryzae, Xanthomonas vesicatoria*); Erwinia (for example *Erwinia amylovora*); and viruses, such as, for example, the Tobacco Mosaic Virus.

The compounds of the invention can be used to protect plants of various useful crops.

The following species of plants, for example, are suitable for the use within the scope of the invention of compounds of formula I of the invention:

cereals (wheat, barley, rye, oats, rice, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (flowers, shrubs, deciduous trees and conifers). This list does not constitute a limitation.

The following plants are to be regarded as especially suitable target crops for the application of the process of the invention: marrows, tobacco, vines, rice, pepper, potatoes, tomatoes, wheat, barley, pears and apples.

The compounds of formula I are obtained by synthesis from 2,6-dihaloisonicotinic acid chlorides, anhydrides or azolides as intermediates:

The compounds of formula I are prepared by reacting:

(a) an isonicotinic acid halide of formula II

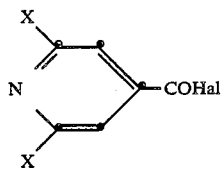

(II)

with an amine of formula III $H_2N-Q_{1-6}$ (III)

in the presence of a base in an inert solvent or without a solvent; or (b) an isonicotinic acid anhydride of formula IV

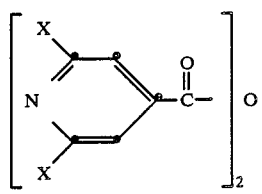

(IV)

an of formula III $H_2N-Q_{1-6}$ (III)

in the presence of a base in an inert solvent or without a solvent; or (c) an isonicotinic acid azolide of formula

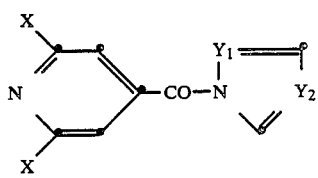

(V)

with an amine of formula III $H_2N-Q_{1-6}$ (III)

in an inert solvent with the separation of an azole; wherein X and $Q_{1-6}$ are as defined for formula I, $Y_1$ and $Y_2$, independently of one another, are each N or CH with $Y_2$ preferably being N, and Hal is halogen, preferably chlorine.

The reaction temperatures in the individual process variants are, for (a) and (b) $-50°$ to $100°$ C., preferably $20°$ to $50°$ C, and for (c) $20°$ to $180°$ C., preferably $50°$ to $130°$ C.

Suitable bases for binding the acid in process variants (a) and (b) are organic and inorganic bases, for example tertiary amines, such as trialkylamines (trimethylamine, triethylamine, tripropylamine etc.), pyridine, pyridine bases (4-dimethylaminopyridine, 4-pyrrolidylaminopyridine etc.) and alcoholates, such as, for example, potassium tert.butoxide, oxides and hydroxides, carbonates and hydrogen carbonates of alkali metals and alkaline earth metals, and also alkali metal acetates. Suitable solvents and diluents that are inert towards the reactions are used as reaction media in process variants (a) and (b) in accordance with the respective reaction conditions. The following may be mentioned as examples: aliphatic and aromatic hydrocarbons, such as benzene, toluene, xylenes, petroleum ether; halogenated hydrocarbons, such as chlorobenzene, methylene chloride, ethylene chloride, chloroform, carbon tetrachloride, tetrachloroethylene; ethers and ethereal compounds, such as dialkyl ethers (diethyl ether, diisopropyl ether, tert.-butyl methyl ether etc.) anisole, dioxan, tetrahydrofuran; nitriles, such as acetonitrile, amide; dimethyl sulfoxide; ketones, such as acetone, diethyl ketone, methyl ethyl ketone; and also mixtures of such solvents with one another.

Reactions of acid chlorides and anhydrides with amines are described in Houben-Weyl, Vol. 18, page 655, and transamidation is described in Angew. Chemie 1962, page 413/412.

The preparation of the starting materials, such as acid chlorides and anhydrides, is familiar to the person skilled in the art and known from the specialist literature (for example Houben-Weyl 5/3, p. 925).

The preparation of the compounds of formula V

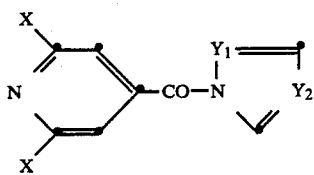

used as starting materials is carried out by reacting a compound of formula II

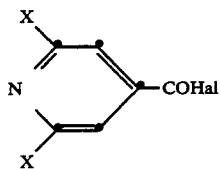

with an azole of formula VI

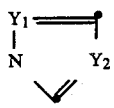

in an inert solvent in the presence of a base, X having the meanings given for formula I, Hal being halogen, preferably chlorine, and $Y_1$ and $Y_2$, independently of one another, each being N or CH.

The reaction temperatures for the above-described synthesis are from $-50°$ to $200°$ C, preferably from $10°$ to $100°$ C.

Suitable bases and solvents are those mentioned for the preparation of compounds of formula I.

Reactions of acid halides with azoles are described in Angew. Chemie 1962, p. 409–411.

The starting materials of formula V

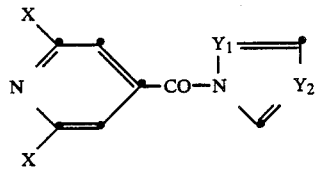

in which X in ortho/ortho'-position are equal and represent fluorine, chlorine, bromine or iodine and $Y_1$ and $Y_2$, independently of one another, are each N or CH, are valuable intermediates for the preparation of the compounds of formula I of the invention. The compounds of formula V are novel substances that also have a protecting activity against the mentioned phytopathogens. The present invention relates also to those compounds.

The microbicidal compositions that are used within the scope of the invention for protecting plants against disease and that contain the compounds of formula I as active ingredients are to be considered as part of the invention.

The compounds of formula I are normally used in the form of compositions and can be applied to the plant or crop area to be treated, simultaneously or in succession, with further compounds. These further compounds can be fertilisers or micronutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

One method of applying a compound of formula I or an agrochemical composition containing at least one of those compounds is application to the plant (foliar application). The compounds of formula I can, however, also penetrate the plant through the roots via the soil (soil application) if the locus of the plant is impregnated with a liquid formulation, or if the compounds are applied in solid form to the soil, for example in granular form. The compounds of formula I may, however, also be applied to seeds (coating), either by impregnating the seeds with a liquid formulation of the compound, or coating them with a solid formulation (dressing). In addition, in special cases further types of application are possible, for example the selective treatment of the plant stems or buds.

The compounds of formula I are used in unmodified form or, preferably, together with the adjuvants conventionally employed in the art of formulation, and are for this purpose advantageously formulated in known manner e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 100 g to 600 g a.i./ha.

The formulations, i.e. the compositions, preparations or mixtures containing the compound (active ingredient) of formula I and, where appropriate, a solid or liquid adjuvant, are prepared by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol ethylene glycol, ethylene glycol monomethyl or monoethyl ether, ketones such as cyclo-hexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Cationic surfactants are especially quaternary ammonium salts that contain as N-substituent at least one alkyl radical having from 8 to 22 carbon atoms and as further substituents lower, unsubstituted or halogenated alkyl, benzyl or hydroxy-lower alkyl radicals. Both so-called water-soluble soaps and also water-soluble synthetic surface-active compounds are suitable anionic surfactants. Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil.

Suitable synthetic surfactants are especially fatty alcohol sulfonates, fatty alcohol sulfates, sulfonated benzimidazole derivatives or alkylsulfonates. The fatty alcohol sulfonates or sulfates are usually in the form of alkali metal salts, alkaline earth metal salts or unsubstituted or substituted ammonium salts and contain an alkyl radical having from 8 to 22 carbon atoms.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

The compositions may also contain further auxiliaries, such as stabilisers, antifoams, viscosity regulators, binders, tackifiers as well as fertilisers or other active ingredients for achieving special effects.

The agrochemical compositions usually contain 0.1 to 99 % by weight, preferably 0.1 to 95 % by weight, of a compound of formula I, 99.9 to 1 % by weight, preferably 99.8 to 5 % by weight, of a solid or liquid adjuvant, and 0 to 25 % by weight, preferably 0.1 to 25 % by weight, of a surfactant.

The following Examples serve to illustrate the invention without implying any limitation.

1. Preparation Examples

Example 1.1

(a) Precursor: Preparation of N-(2,6-dichloroisonicotinoyl)-imidazole

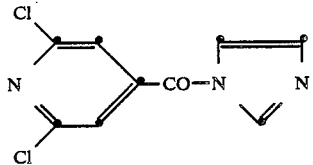

6.8 g (0.10 mole) of imidazole and 15.3 ml (0.11 mole) of triethylamine are stirred in 100 ml of tetrahydrofuran. While cooling at 25°–30° C., a solution of 23.1 g (0.11 mole) of 2,6-dichloroisonicotinic acid chloride in 20 ml of tetrahydrofuran is then added dropwise, triethylamine hydrochloride separating. This is filtered off with suction and the filtrate is concentrated to 26.4 g of crude product. Recrystallisation from ethyl acetate yields 20.1 g (83 % of the theoretical amount) of pure substance; m.p. 148°–151° C.

(b) End product: Preparation of N-[(2-isopropoxy-5-chloro)-pyrimidin-4-yl]-2,6-dichloroisonicotinic acid amide

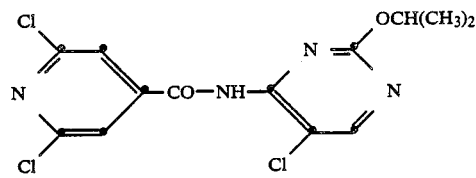

131.3 g (0.70 mole) of 2-isopropoxy-4-amino-5-chloropyrimidine and 176.4 g (0.73 mole) of N-(2,6-dichloroisonicotinoyl)-imidazole are suspended in 500 ml of toluene. The suspension is heated to reflux temperature and boiled for 1 hour. After cooling, the reaction mixture is extracted with ethyl acetate and water, and then the ethyl acetate phase is washed twice with water in order to remove completely the imidazole that has formed. The organic phase is dried over $Na_2SO_4$ and concentrated in a rotary evaporator to 246 g of crude product, which is purified by separating by column chromatography (silica gel; eluant mixture: n-hexane/ethyl acetate 4:1). 83 g (32.8 % of the theoretical amount) of pure product and 130 g of mixed fractions containing educt that is difficult to remove are obtained. This mixture is again separated by column chromatography to yield a further 78 g (30.8 % of the theoretical amount) of pure substance. Recrystallisation of the 83 g of product from 400 ml of diethyl ether yields 57 g of crystalline compound having a melting point of 106°–108° C.

Example 1.2: Preparation of N-[(2-dimethylamino-6-methoxy)-pyrimidin-4-yl]-2,6-dichloroisonicotinic acid amide

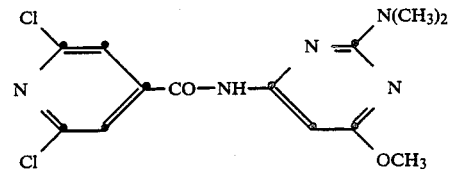

3.00 g (0.078 mole) of 2-dimethylamino-4-amino-6-methoxypyrimidine are dissolved in a mixture of 10 ml of pyridine and 10 ml of tetrahydrofuran. While cooling, a solution of 5.26 g (0.025 mole) of 2,6-dichloroisonicotinic acid chloride in 20 ml of tetrahydrofuran is added dropwise at 20° C., pyridine hydrochloride separating. The batch is further stirred for one hour at 20° C. and then extracted with ethyl acetate and water with the addition of acetic acid at pH 6–7. The organic phase is separated off, dried over $Na_2SO_4$ and concentrated to the crude product, which is then chromatographed over silica gel with a mixture of hexane/ethyl acetate 4:1. Concentration of the pure fractions yields 5.21 g of substance, which is boiled in 30 ml of acetonitrile. The batch is filtered with suction at 20° C. and dried at 60° C. in vacuo to yield 3.51 g (57.6 %

Example 1.3

Precursor: Preparation of N-(2,6-dichloroisonicotinoyl)-triazole

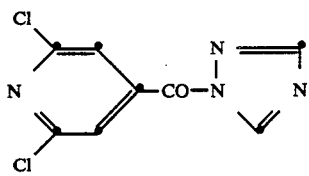

6.90 g (0.10 mole) of triazole and 12.12 g (0.12 mole) of triethylamine are dissolved in 150 ml of tetrahydrofuran, molecular sieve (0.4 nm, Merck) is added, and the batch is left to stand for two days at 20° C. A solution of 23.15 g (0.11 mole) of 2,6-dichloroisonicotinic acid chloride in 30 ml of tetrahydrofuran dried with molecular sieve is then slowly added dropwise. The reaction is exothermic; the mixture is maintained at 15°–25° C. by cooling. The separated triethylamine hydrochloride is filtered off with suction and the filtrate is concentrated in a rotary evaporator to 25.2 g of crude product. Recrystallisation from a mixture of 50 ml of anhydrous toluene and 30 ml of anhydrous cyclohexane yields 12.3 g (50.9% of the theoretical amount) of N-(2,6-dichloroisonicotinoyl)-triazole. It is possible by concentrating the mother liquor to isolate a further 6.5 g (27% of the theoretical amount) of substance. M.p. 110°–113° C.

(b) End product: Preparation of N-[(2-n-propyl-6-chloro)-pyrimidin-4-yl]-2.6-dichloroisonicotinic acid amide

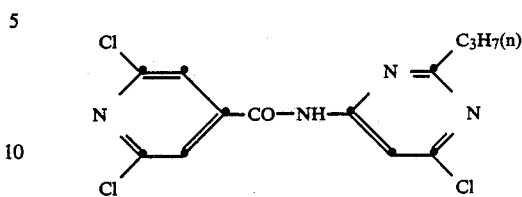

2.23 g (0.013 mole) of 2-n-propyl-4-amino-6-chloropyrimidine and 3.40 g (0.014 mole) of N-(2,6-dichloroisonicotinoyl)-triazole are weighed into 15 ml of toluene dried with molecular sieve and the batch is boiled at reflux for 1.5 hours with the exclusion of atmospheric moisture. At first a clear solution forms, which later becomes turbid. After cooling, the batch is extracted with water and ethyl acetate in a separating funnel in order to remove the product formed. After concentrating the organic phase, the crude product is chromatographed over a column of silica gel with a mixture of hexane/ethyl acetate 3:1. Concentration of the pure fractions and recrystallisation of the residue from a mixture of 3 ml of ethyl acetate and 10 ml of hexane yields 3.34 g (74.3% of the theoretical amount) of product. By further recrystallisation of the mother liquor, 0.90 g (20.0% of the theoretical amount) of a second fraction is obtained. Both substances have a melting point of 134°–135° C.

The compounds listed in the following are obtained in accordance with the described methods of preparation.

TABLE 1

| No. | X | $R_1'$ | $R_2'$ | $R_3'$ | physical data |
|---|---|---|---|---|---|
| 1.1 | Cl | $OCH(CH_3)_2$ | Cl | H | m.p. 106–108° C. |
| 1.2 | Cl | $N(CH_3)_2$ | H | $OCH_3$ | m.p. 200–202° C. |
| 1.3 | Cl | $CH_2CH_2CH_3$ | H | Cl | m.p. 134–135° C. |
| 1.4 | Cl | $OCH_3$ | Cl | H | m.p. 148° C. |
| 1.5 | Cl | H | $CH_3$ | Cl | m.p. 176–178° C. |
| 1.6 | Cl | H | $C_2H_5$ | Cl | m.p. 145–147° C. |
| 1.7 | Cl | H | $CH_2CH_2CH_3$ | Cl | m.p. 149–151° C. |
| 1.8 | Cl | H | H | Cl | m.p. 171–172° C. |
| 1.9 | Cl | H | H | $SCH_3$ | m.p. 160–165° C. |
| 1.10 | Cl | H | H | $OCH_3$ | |
| 1.11 | Cl | H | H | $N(CH_3)_2$ | |
| 1.12 | Cl | H | H | $OCH(CH_3)_2$ | |
| 1.13 | Cl | H | H | $SC(CH_3)_3$ | |
| 1.14 | Cl | H | H | $OCH_2CH=CH_2$ | |
| 1.15 | Cl | H | H | $OCH_2C\equiv CH$ | |
| 1.16 | Br | $OCH_3$ | Cl | H | |
| 1.17 | Br | $OCH(CH_3)_2$ | Cl | H | |
| 1.18 | Cl | $CH_3$ | H | $CH_3$ | m.p. 142–144° C. |
| 1.19 | Br | $CH_3$ | H | $CH_3$ | |
| 1.20 | Cl | $CH_3$ | $CH_3$ | Cl | m.p. 154–155° C. |
| 1.21 | Cl | $CH_3$ | $CH_3$ | $OC_2H_5$ | |
| 1.22 | Cl | $CH_3$ | $CH_3$ | $SCH_2CH_2CH_3$ | |
| 1.23 | Cl | $CH_3$ | H | Cl | |
| 1.24 | Cl | $CH_3$ | H | $OCH(CH_3)C_2H_5$ | |
| 1.25 | Cl | $CH_3$ | H | $SC_2H_5$ | |
| 1.26 | Cl | $CH_3$ | H | $N(C_2H_5)_2$ | |
| 1.27 | Cl | $C_2H_5$ | $CH_3$ | Cl | m.p. 168–169° C. |
| 1.28 | Br | $C_2H_5$ | $CH_3$ | Cl | |
| 1.29 | Cl | $C_2H_5$ | $CH_3$ | $OCH_3$ | |

TABLE 1-continued

[Structure diagram of compound with X, N, CO-NH, R₁', R₂', R₃' substituents]

| No. | X | R₁' | R₂' | R₃' | physical data |
|---|---|---|---|---|---|
| 1.30 | Cl | $C_2H_5$ | $CH_3$ | $OC_2H_5$ | |
| 1.31 | Cl | $C_2H_5$ | $CH_3$ | $OCH_2CH=CH_2$ | |
| 1.32 | Cl | $C_2H_5$ | $CH_3$ | F | |
| 1.33 | Cl | $C_2H_5$ | $CH_3$ | $SCH_3$ | |
| 1.34 | Cl | $C_2H_5$ | $CH_3$ | $N(CH_3)_2$ | |
| 1.35 | Cl | $C_2H_5$ | $C_2H_5$ | Cl | m.p. 115–116° C. |
| 1.36 | Br | $C_2H_5$ | $C_2H_5$ | Cl | |
| 1.37 | Cl | $C_2H_5$ | $C_2H_5$ | $OCH_3$ | |
| 1.38 | Cl | $C_2H_5$ | $C_2H_5$ | $OCH(CH_3)_2$ | |
| 1.39 | Cl | $C_2H_5$ | $C_2H_5$ | $SCH(CH_3)_2$ | |
| 1.40 | Cl | $C_2H_5$ | $C_2H_5$ | $OCH_2CF_3$ | |
| 1.41 | Cl | $CH_2CH_2CH_3$ | $CH_3$ | Cl | m.p. 125–126° C. |
| 1.42 | Cl | $CH(CH_3)_2$ | $CH_3$ | Cl | |
| 1.43 | Cl | $C(CH_3)_3$ | $CH_3$ | Cl | |
| 1.44 | Cl | $CH_3$ | $C_2H_5$ | Cl | |
| 1.45 | Cl | $CH_2CH_2CH_3$ | $C_2H_5$ | Cl | |
| 1.46 | Cl | $CH(CH_3)_2$ | $C_2H_5$ | Cl | |
| 1.47 | Cl | $(CH_2)_5CH_3$ | $C_2H_5$ | Cl | |
| 1.48 | Cl | $C(CH_3)_3$ | $C_2H_5$ | Cl | |
| 1.49 | Cl | $CH_3$ | $CH_2CH_2CH_3$ | Cl | |
| 1.50 | Cl | $CH_3$ | $CH_2CH_2CH_3$ | $OCH_3$ | |
| 1.51 | Cl | $CH_3$ | $C_2H_5$ | $SCH_3$ | |
| 1.52 | Cl | $N(CH_3)_2$ | $CH_3$ | Cl | |
| 1.53 | Cl | $N(CH_3)_2$ | H | Cl | m.p. 195–197° C. |
| 1.54 | Cl | $N(CH_3)_2$ | $CH_3$ | $SCH_3$ | |
| 1.55 | Cl | $C_2H_5$ | H | Cl | m.p. 132–134° C. |
| 1.56 | Cl | $CH(CH_3)_2$ | H | Cl | m.p. 137–138° C. |
| 1.57 | Cl | $CH(CH_3)_2$ | H | $CH_3$ | m.p. 117–119° C. |
| 1.58 | Cl | $CH(CH_3)_2$ | H | $OC_2H_5$ | m.p. 119–120° C. |
| 1.59 | Cl | $CH(CH_3)_2$ | H | $OCH_2CH(CH_3)_2$ | m.p. 110–111° C. |
| 1.60 | Cl | $CH(CH_3)_2$ | H | $SCH(CH_3)_2$ | m.p. 144–145° C. |
| 1.61 | Br | $CH(CH_3)_2$ | H | $SCH_3$ | |
| 1.62 | Br | $CH(CH_3)_2$ | H | $OC_2H_5$ | |
| 1.63 | Cl | $CH(CH_3)_2$ | H | $SC_2H_5$ | m.p. 169–171° C. |
| 1.64 | Cl | $CH(CH_3)_2$ | H | $OCH(CH_3)C_2H_5$ | $n_D^{50}$ 1.552 |
| 1.65 | Cl | $CH(CH_3)_2$ | H | $N(C_2H_5)_2$ | |
| 1.66 | Cl | $CH(CH_3)_2$ | H | —N[morpholino ring with O] | |
| 1.67 | Cl | $CH(CH_3)_2$ | H | —N[imidazole ring with N] | m.p. 229–231° C. |
| 1.68 | Cl | H | H | —N[piperidine ring] | |
| 1.69 | Cl | H | H | $SC_2H_5$ | |
| 1.70 | Cl | H | H | —N[2,6-dimethylmorpholino ring with O and two $CH_3$] | |
| 1.71 | Cl | cyclo-$C_3H_5$ | H | F | m.p. 98–101° C. |
| 1.72 | Br | cyclo-$C_3H_5$ | H | F | |
| 1.73 | Cl | cyclo-$C_3H_5$ | H | Cl | m.p. 150° C.(decomp.) |
| 1.74 | Cl | cyclo-$C_3H_5$ | $CH_3$ | Cl | m.p. 156–158° C. |
| 1.75 | Cl | cyclo-$C_3H_5$ | $C_2H_5$ | Cl | m.p. 143–144° C. |

TABLE 1-continued

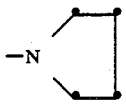

| No. | X | R$_1$' | R$_2$' | R$_3$' | physical data |
|---|---|---|---|---|---|
| 1.76 | Cl | OCH(CH$_3$)$_2$ | Br | H | |
| 1.77 | Cl | OCH(CH$_3$)$_2$ | F | H | |
| 1.78 | Cl | OCH(CH$_3$)$_2$ | J | H | |
| 1.79 | Cl | Cl | F | H | m.p. 172–174° C. |
| 1.80 | Cl | Cl | Cl | H | m.p. 244–246° C. |
| 1.81 | Cl | C$_6$H$_5$ | H | Cl | |
| 1.82 | Cl | C$_6$H$_5$ | H | SCH(CH$_3$)C$_2$H$_5$ | |
| 1.83 | Cl | C$_6$H$_5$ | H | OCH$_3$ | |
| 1.84 | Cl | C$_6$H$_5$ | H | SCH$_2$CH$_2$CH$_3$ | |
| 1.85 | Cl | Cl | Cl | Cl | m.p. 184–186° C. |
| 1.86 | Cl | H | H | H | |
| 1.87 | Cl | OCH$_3$ | Cl | CH$_3$ | |
| 1.88 | Cl | OCH$_3$ | Cl | C$_2$H$_5$ | |
| 1.89 | Cl | OCH$_3$ | F | H | m.p. 132–134° C. |
| 1.90 | Cl | C$_6$H$_5$ | H | 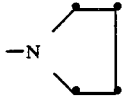 | |
| 1.91 | Cl | H | H | 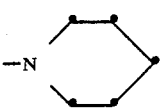 | |
| 1.92 | Cl | Cl | H | CH$_2$CH$_2$CH$_3$ | m.p. 93–94° C. |
| 1.93 | Cl | Cl | H | C$_2$H$_5$ | |
| 1.94 | Cl | Cl | H | CH$_3$ | m.p. 200–204° C. |
| 1.95 | Br | Cl | Cl | CH$_3$ | |
| 1.96 | Cl | OC$_2$H$_5$ | Cl | H | m.p. 140–141° C. |
| 1.97 | Cl | OC$_2$H$_5$ | F | H | |
| 1.98 | Cl | OCH(CH$_3$)$_2$ | Cl | CH$_3$ | |
| 1.99 | Br | OCH(CH$_3$)$_2$ | Cl | C$_2$H$_5$ | |
| 1.100 | Cl | OCH$_2$CH$_2$CH$_3$ | Cl | H | m.p. 105–107° C. |
| 1.101 | Cl | SCH$_3$ | Cl | H | m.p. 124–125° C. |
| 1.102 | Cl | SCH$_3$ | Cl | CH$_3$ | |
| 1.103 | Cl | OCH$_2$CF$_3$ | Cl | H | m.p. 50–55° C. |
| 1.104 | Cl | OCH$_2$CH(CH$_3$)$_2$ | Cl | H | |
| 1.105 | Cl | SC$_2$H$_5$ | Cl | H | |
| 1.106 | Cl | OCH(CH$_3$)$_2$ | Cl | CH$_2$CH$_2$CH$_3$ | |
| 1.107 | Cl | OC(CH$_3$)$_3$ | Cl | H | |
| 1.108 | Cl | OCH(CH$_3$)C$_2$H$_5$ | Cl | H | |
| 1.109 | Cl | SCH$_3$ | CH$_3$ | Cl | m.p. 182–187° C. |
| 1.110 | Br | SCH$_3$ | CH$_3$ | OC$_2$H$_5$ | |
| 1.111 | Cl | SCH$_3$ | CH$_3$ | OCH$_3$ | |
| 1.112 | Cl | SCH$_3$ | H | Cl | m.p. 84–89° C. |
| 1.113 | Cl | SCH$_3$ | H | OCH$_3$ | m.p. 227–229° C. |
| 1.114 | Cl | CF$_3$ | H | Cl | oil |
| 1.115 | Cl | H | NO$_2$ | OCH$_3$ | |
| 1.116 | Cl | H | NO$_2$ | SCH$_2$CH=CH$_2$ | |
| 1.117 | Cl | H | NO$_2$ | SC(CH$_3$)$_3$ | |
| 1.118 | Cl | SCH(CH$_3$)$_2$ | Cl | H | |
| 1.119 | Cl | N(CH$_3$)$_2$ | Cl | H | |
| 1.120 | Cl | CH$_2$CH$_2$OCH$_3$ | H | Cl | m.p. 176–178° C. |
| 1.121 | Cl | OCH$_3$ | H | H | |
| 1.122 | Cl | OCH(CH$_3$)$_2$ | H | H | |
| 1.123 | Cl | OCH$_3$ | Br | H | |
| 1.124 | Cl | OCH$_3$ | NO$_2$ | H | |
| 1.125 | Cl | OC$_6$H$_5$ | Cl | H | |
| 1.126 | Cl | SC$_6$H$_5$ | Cl | H | |
| 1.127 | Cl | | Cl | H | |

TABLE 1-continued

| No. | X | R₁' | R₂' | R₃' | physical data |
|---|---|---|---|---|---|
| 1.128 | Cl | $-N\begin{pmatrix}CH_3\\ \\CH_3\end{pmatrix}O$ | Cl | H | |
| 1.129 | Cl | C(CH₃)₃ | H | Cl | m.p. 131–133° C. |
| 1.130 | Cl | C(CH₃)₃ | H | SC₆H₅ | |
| 1.131 | Cl | H | H | SC₆H₅ | |
| 1.132 | Cl | H | H | OC₆H₅ | |
| 1.133 | Cl | OCH₂CH=CH₂ | Cl | H | |
| 1.134 | Cl | OCH₂C≡CH | Cl | H | |
| 1.135 | Cl | SCH₂CH=CH₂ | Cl | H | |
| 1.136 | Cl | Cl | H | C₆H₅ | |
| 1.137 | Cl | OCH₃ | H | C₆H₅ | |
| 1.138 | Cl | OC(CH₃)₃ | H | C₆H₅ | |
| 1.139 | Br | C₂H₅ | CH₃ | Cl | m.p. 145–146° C. |
| 1.140 | Br | OCH(CH₃)₂ | Cl | H | |
| 1.141 | F | OCH(CH₃)₂ | Cl | H | |
| 1.142 | J | OCH(CH₃)₂ | Cl | H | |
| 1.143 | Cl | OCH₃ | J | H | |
| 1.144 | Cl | OCH₃ | Br | H | |
| 1.145 | Cl | CH₂CH₂CH₃ | H | $-N\begin{matrix}N=\\ \ \ \ \ \ \ \ \ \\N\end{matrix}$ | m.p. 234–235° C. |
| 1.146 | Br | OCH₃ | Cl | H | |
| 1.147 | F | OCH₃ | Cl | H | |
| 1.148 | J | OCH₃ | Cl | H | |
| 1.149 | Cl | CH₃ | H | CF₃ | m.p. 149–150° C. |
| 1.150 | Cl | CH₃ | COOC₂H₅ | CH₃ | |
| 1.151 | Cl | CH₂C₆H₅ | COOCH₃ | H | |
| 1.152 | Cl | CH₂C₆H₅ | H | CN | |
| 1.153 | Cl | CH₃ | CN | H | |
| 1.154 | Cl | Cl | CN | SCH₃ | |
| 1.155 | Cl | CH₃ | J | CH₃ | |
| 1.156 | Cl | OCH₃ | H | OCH₃ | m.p. 162–164° C. |
| 1.157 | Cl | N(CH₃)₂ | NO₂ | H | |
| 1.158 | Cl | H | NO₂ | N(CH₃)₂ | |
| 1.159 | Cl | Cl | CH₂C₆H₅ | H | |
| 1.160 | Cl | Cl | CH₂C₆H₅ | Cl | |
| 1.161 | Cl | H | Br | H | |
| 1.162 | Cl | C₂H₅ | H | Br | |
| 1.163 | Cl | CH₃ | CH₂Br | H | |
| 1.164 | Cl | Cl | CH₂Cl | H | |
| 1.165 | Cl | CH₃ | (CH₂)₅CH₃ | Cl | m.p. 135–137° C. |
| 1.166 | Cl | CH₃ | (CH₂)₃CH₃ | Cl | |
| 1.167 | Cl | cyclo-C₃H₅ | CH₃ | Cl | m.p. 198–199° C. |
| 1.168 | Cl | cyclo-C₃H₅ | C₂H₅ | Cl | m.p. 143–144° C. |
| 1.169 | Cl | H | CH₂CH=CH₂ | Cl | m.p. 117–118° C. |
| 1.170 | Cl | CH₃ | C₂H₅ | Cl | m.p. 133–135° C. |
| 1.171 | Cl | CH₃ | CH₂CH=CH₂ | Cl | m.p. 123–124° C. |
| 1.172 | Cl | CH₃ | C₂H₅ | H | m.p. 131–133° C. |
| 1.173 | Cl | CH₃ | CH₂—C₆H₅ | Cl | m.p. 138–139° C. |
| 1.174 | Cl | H | CH₂—C₆H₅ | Cl | m.p. 128–129° C. |
| 1.175 | Cl | CH₃ | CH₃ | Cl | m.p. 154–155° C. |
| 1.176 | Cl | C₂H₅ | CH₃ | F | m.p. 140–142° C. |
| 1.177 | Cl | CH₃ | C₃H₇(n) | Cl | m.p. 185–187° C. |
| 1.178 | Cl | H | (CH₂)₃CH₃ | Cl | m.p. 103–105° C. |
| 1.179 | Cl | CH(CH₃)₂ | CH₃ | Cl | m.p. 131–133° C. |
| 1.180 | Cl | H | C₂H₅ | F | m.p. 136–138° C. |
| 1.181 | Cl | C₂H₅ | C₂H₅ | F | m.p. 102–104° C. |
| 1.182 | Cl | C₂H₅ | C₂H₅ | H | m.p. 98–99° C. |
| 1.183 | Br | H | C₂H₅ | Cl | m.p. 164–167° C. |

TABLE 2

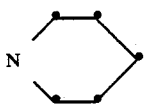

| No. | X | $R_1'$ | $R_2'$ | $R_3'$ | physical data |
|---|---|---|---|---|---|
| 2.1 | Cl | H | H | H | m.p. 214–216° C. |
| 2.2 | F | H | H | H | |
| 2.3 | Cl | Cl | H | Cl | m.p. 198–199° C. |
| 2.4 | Cl | Cl | H | $OCH_3$ | |
| 2.5 | Cl | Cl | H | $OC_2H_5$ | |
| 2.6 | Cl | Cl | H | $OCH_2CH=CH_2$ | m.p. 160° C. |
| 2.7 | Cl | Cl | H | $OCH_2C\equiv CH$ | m.p. 148–149° C. |
| 2.8 | Cl | Cl | H | $SCH_3$ | |
| 2.9 | Cl | Cl | H | $SC_6H_5$ | |
| 2.10 | Cl | H | H | $OC_3H_7(n)$ | |
| 2.11 | Cl | H | H | $SC_2H_5$ | |
| 2.12 | Cl | H | Cl | Cl | |
| 2.13 | Cl | H | Cl | $OC_2H_5$ | m.p. 162–165° C. |
| 2.14 | F | H | Cl | $OC_2H_5$ | |
| 2.15 | Cl | H | Br | $OCH_3$ | |
| 2.16 | Cl | H | Br | Cl | |
| 2.17 | Cl | $OCH_3$ | $NO_2$ | $OCH_3$ | |
| 2.18 | Cl | $CH_3$ | H | $CH_3$ | m.p. 165–168° C. |
| 2.19 | F | $CH_3$ | H | $CH_3$ | |
| 2.20 | Br | $CH_3$ | H | $CH_3$ | |
| 2.21 | Cl | $CH_3$ | H | Cl | m.p. 178–182° C. |
| 2.22 | Cl | $CH_3$ | H | $N(CH_3)_2$ | |
| 2.23 | Cl | $CH_3$ | H | $SCH(CH_3)_2$ | |
| 2.24 | Cl | $CH_3$ | H | $SCH_2C_6H_5$ | |
| 2.25 | Cl | $CH_3$ | H | $OC_6H_5$ | |
| 2.26 | Cl | $CH_3$ | H | 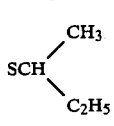 | |
| 2.27 | Cl | $CH_3$ | H | $OCHF_2$ | m.p. 160–162° C. |
| 2.28 | F | $CH_3$ | H | $OCHF_2$ | |
| 2.29 | Cl | $CH_3$ | H | $C_2H_5$ | |
| 2.30 | Cl | $CH_3$ | H | $C_3H_7(n)$ | |
| 2.31 | Cl | $CH_3$ | H | cyclo-$C_3H_5$ | m.p. 145–147° C. |
| 2.32 | Cl | $C_2H_5$ | H | Cl | |
| 2.33 | Br | $CH(CH_3)_2$ | H | Cl | |
| 2.34 | J | $CH(CH_3)_2$ | H | Cl | |
| 2.35 | F | $CH(CH_3)_2$ | H | Cl | |
| 2.36 | Cl | $CH(CH_3)_2$ | H | Cl | m.p. 174–176° C. |
| 2.37 | Cl | Cl | Cl | Cl | |
| 2.38 | Cl | Cl | Br | Cl | |
| 2.39 | Cl | $CH_2CH_2CH_3$ | H | Cl | m.p. 135–137° C. |
| 2.40 | Cl | $CH_2CH_2CH_3$ | H | $OCH_3$ | |
| 2.41 | Cl | $CH_2CH_2CH_3$ | H | $SCH{<}^{CH_3}_{C_2H_5}$ | |
| 2.42 | Cl | $CH_2CH_2CH_3$ | H | $OCH_2CF_3$ | |
| 2.43 | Cl | Cl | H | $OC_6H_5$ | |
| 2.44 | Cl | $CH(CH_3)_2$ | H | $OCH_3$ | |
| 2.45 | Br | $CH(CH_3)_2$ | H | $OCH(CH_3)_2$ | |
| 2.46 | Cl | $CH(CH_3)_2$ | H | $OCH(CH_3)_2$ | |
| 2.47 | Cl | $CH(CH_3)_2$ | H | $SC_2H_5$ | |
| 2.48 | Cl | $CH(CH_3)_2$ | H | 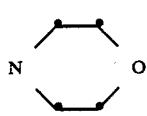 | |
| 2.49 | Cl | $CH_2COOC_2H_5$ | H | $OC_2H_5$ | m.p. 111–113° C. |
| 2.50 | Cl | $OCH_3$ | H | $OCH_3$ | |
| 2.51 | Cl | $OCH(CH_3)_2$ | H | $OCH(CH_3)_2$ | |
| 2.52 | Cl | $SC_2H_5$ | H | $SC_2H_5$ | |
| 2.53 | Cl | $SC_6H_5$ | H | $SC_6H_5$ | |
| 2.54 | Cl | $OC_2H_5$ | H | $SC_3H_7(n)$ | |

TABLE 2-continued

[Structure: pyrimidine-CONH-pyrimidine with X, R$_1'$, R$_2'$, R$_3'$ substituents]

| No. | X | R$_1'$ | R$_2'$ | R$_3'$ | physical data |
|---|---|---|---|---|---|
| 2.55 | Cl | N(C$_2$H$_5$) | H | SCH$_2$C$_6$H$_5$ | |
| 2.56 | Cl | CH$_2$Cl | H | Cl | m.p. 135–138° C. |
| 2.57 | Cl | CH$_3$ | CH$_3$ | Cl | |
| 2.58 | Cl | CH$_3$ | C$_2$H$_5$ | Cl | |
| 2.59 | Cl | CH$_3$ | C$_3$H$_7$ | Cl | |
| 2.60 | Cl | CH$_3$ | CH$_3$ | OC$_3$H$_7$(n) | |
| 2.61 | Cl | CH$_3$ | C$_2$H$_5$ | SC$_2$H$_5$ | |
| 2.62 | Cl | CH$_3$ | CH$_3$ | CH$_3$ | |
| 2.63 | Cl | CH$_3$ | C$_2$H$_5$ | CH$_3$ | |
| 2.64 | Cl | CH$_3$ | C$_3$H$_7$(n) | CH$_3$ | |
| 2.65 | Cl | CH$_3$ | CH(CH$_3$)$_2$ | CH$_3$ | |
| 2.66 | Cl | CH$_3$ | Cl | CH$_3$ | |
| 2.67 | Cl | CH$_3$ | OCH$_3$ | CH$_3$ | |
| 2.68 | Cl | CH$_3$ | SCH$_3$ | CH$_3$ | |
| 2.69 | Cl | CH$_3$ | SCH(CH$_3$)$_2$ | CH$_3$ | |
| 2.70 | Cl | CH$_3$ | F | CH$_3$ | |
| 2.71 | Cl | CH$_3$ | OC$_6$H$_5$ | CH$_3$ | |
| 2.72 | Cl | CH$_3$ | N(C$_2$H$_5$)$_2$ | CH$_3$ | |
| 2.73 | Cl | CH$_3$ | [morpholino-N ring] | CH$_3$ | |
| 2.74 | Cl | CH$_3$ | [2,6-dimethylmorpholino] | CH$_3$ | |
| 2.75 | Cl | CH$_3$ | CH$_3$ | H | |
| 2.76 | Cl | CH$_3$ | C$_2$H$_5$ | H | |
| 2.77 | Cl | C$_2$H$_5$ | CH$_3$ | H | |
| 2.78 | Cl | CH(CH$_3$)$_2$ | H | H | |
| 2.79 | Cl | C$_3$H$_7$(n) | H | H | |
| 2.80 | Cl | CH$_3$ | H | H | |
| 2.81 | Cl | Cl | CH$_3$ | Cl | |
| 2.82 | Cl | F | CH$_3$ | F | |
| 2.83 | Cl | Cl | Cl | OCH$_3$ | |
| 2.84 | Cl | Cl | Cl | SC$_2$H$_5$ | |
| 2.85 | Cl | CH$_3$ | H | F | |
| 2.86 | Cl | CH$_2$CH$_2$CH$_3$ | H | F | |
| 2.87 | Cl | CH(CH$_3$)$_2$ | H | F | |
| 2.88 | Cl | CH$_3$ | H | OCH$_2$CF$_3$ | |
| 2.89 | Cl | Cl | SCH$_3$ | Cl | |
| 2.90 | Cl | CH(OC$_2$H$_5$)$_2$ | H | Cyclo-C$_3$H$_5$ | m.p. 100–101° C. |
| 2.91 | Cl | C$_2$H$_5$ | H | C$_2$H$_5$ | m.p. 117–119° C. |
| 2.92 | Cl | CH$_2$OCH$_3$ | H | Cyclo-C$_3$H$_5$ | m.p. 115–118° C. |
| 2.93 | Cl | Cyclo-C$_3$H$_5$ | H | Cyclo-C$_3$H$_5$ | m.p. 138–140° C. |
| 2.94 | Cl | C$_2$H$_5$ | H | CH$_2$OCH$_3$ | m.p. 89–91° C. |
| 2.95 | Cl | CH$_3$ | H | [1-methylcyclopropyl] | m.p. 159–161° C. |

TABLE 3

| No. | X | R₁' | R₂' | R₃' | physical data |
|---|---|---|---|---|---|
| 3.1 | Cl | H | H | H | m.p. 161–162° C. |
| 3.2 | Cl | H | Cl | Cl | m.p. 224–225° C. |
| 3.3 | Cl | H | Cl | OCH₃ | |
| 3.4 | Cl | H | Cl | OC₂H₅ | |
| 3.5 | Cl | H | Cl | OCH₂CF₃ | m.p. 197–198° C. |
| 3.6 | Cl | H | Cl | OCH₂CH=CH₂ | |
| 3.7 | Cl | H | Cl | SCH₃ | m.p. 201–203° C. |
| 3.8 | Cl | H | Cl | SC₆H₅ | |
| 3.9 | F | H | Cl | OCH₃ | |
| 3.10 | Br | H | Cl | OCH₃ | |
| 3.11 | Cl | H | OCH₃ | OCH₃ | |
| 3.12 | Cl | H | SC₃H₇(n) | SC₃H₇(n) | |
| 3.13 | Cl | H | H | Cl | |
| 3.14 | Cl | H | H | OCH₃ | |
| 3.15 | Cl | H | SCH₃ | SCH₃ | |
| 3.16 | Cl | H | OCH₂CF₃ | OCH₂CF₃ | |
| 3.17 | Cl | CH₃ | Cl | Cl | m.p. 230–231° C. |
| 3.18 | Cl | CH₃ | Cl | OCH(CH₃)₂ | |
| 3.19 | Cl | CH₃ | Cl | OCH₂CF₃ | m.p. 197–198° C. |
| 3.20 | Br | CH₃ | Cl | OCH₂CF₃ | |
| 3.21 | Cl | CH₃ | H | OC₂H₅ | m.p. 215–216° C. |
| 3.22 | Cl | H | Cl | OCH₂C₆H₅ | |
| 3.23 | Cl | H | Cl | OC₆H₅ | |
| 3.24 | Cl | H | Cl | N(C₃H₇)₂ | |
| 3.25 | Cl | H | Cl | H | |
| 3.26 | Cl | CH₃ | Cl | OC₂H₅ | m.p. 211–212° C. |
| 3.27 | Cl | CH₃ | —N…O— (ring) | OC₂H₅ | |
| 3.28 | Cl | C₂H₅ | Cl | Cl | |
| 3.29 | Cl | C₂H₅ | H | H | |
| 3.30 | Cl | C₂H₅ | Cl | —N…O— (ring) | |
| 3.31 | Cl | C₂H₅ | Cl | SCH(CH₃)₂ | |
| 3.32 | Cl | C₂H₅ | Cl | N(C₄H₉-n)₂ | |
| 3.33 | Cl | C₂H₅ | Cl | OCH₂CF₃ | m.p. 200–202° C. |
| 3.34 | Cl | CH(CH₃)₂ | H | H | m.p. 176–177° C. |
| 3.35 | Cl | CH(CH₃)₂ | Cl | Cl | m.p. 212–214° C. |
| 3.36 | Cl | CH(CH₃)₂ | Cl | OCH₃ | |
| 3.37 | Cl | CH(CH₃)₂ | Cl | OC₂H₅ | |
| 3.38 | Cl | CH(CH₃)₂ | Cl | OCH₂CF₃ | m.p. 139–141° C. |
| 3.39 | Cl | CH(CH₃)₂ | Cl | OC(CH₃)₃ | |
| 3.40 | Cl | CH(CH₃)₂ | Cl | SCH₃ | m.p. 208–209° C. |
| 3.41 | Cl | CH(CH₃)₂ | Cl | H | |
| 3.42 | Cl | CH(CH₃)₂ | Cl | SCH(CH₃)C₂H₅ | |
| 3.43 | Cl | C(CH₃)₃ | Cl | Cl | m.p. 203–205° C. |
| 3.44 | Cl | C(CH₃)₃ | Cl | H | |
| 3.45 | Cl | C(CH₃)₃ | H | H | |
| 3.46 | Cl | C(CH₃)₃ | Cl | OCH₃ | m.p. 188–191° C. |
| 3.47 | Cl | C(CH₃)₃ | Cl | SCH₃ | |
| 3.48 | Cl | CH₃ | Cl | H | |
| 3.49 | Cl | cyclo-C₃H₅ | Cl | Cl | m.p. 228–230° C. |
| 3.50 | Cl | cyclo-C₃C₅ | H | H | |
| 3.51 | Cl | cyclo-C₃H₅ | Cl | N(CH₃)₂ | |
| 3.52 | Cl | N(CH₃)₂ | Cl | Cl | |
| 3.53 | Cl | N(CH₃)₂ | F | F | |
| 3.54 | Cl | CH₃ | F | F | |
| 3.55 | Cl | C₂H₅ | F | F | |
| 3.56 | Cl | CCl₃ | F | F | |
| 3.57 | Cl | CF₃ | Cl | Cl | |
| 3.58 | Cl | CCl₃ | Cl | Cl | |
| 3.59 | Cl | N(CH₃)₂ | Cl | OCH₃ | |

TABLE 3-continued

| No. | X | $R_1'$ | $R_2'$ | $R_3'$ | physical data |
|---|---|---|---|---|---|
| 3.60 | Cl | N(CH$_3$)$_2$ | Cl | SCH$_3$ | |
| 3.61 | Cl | N(CH$_3$)$_2$ | Cl | OCH(CH$_3$)C$_3$H$_7$ | |
| 3.62 | Cl | N(CH$_3$)$_2$ | Cl | OCH$_2$C≡CH | |
| 3.63 | Cl | N(CH$_3$)$_2$ | Cl | CH$_3$ | |
| 3.64 | Cl | N(CH$_3$)$_2$ | OCH$_3$ | CH$_3$ | |
| 3.65 | Cl | N(CH$_3$)$_2$ | SCH$_3$ | CH$_3$ | |
| 3.66 | Cl | N(CH$_3$)$_2$ | F | CH$_3$ | |
| 3.67 | Cl | Cl | Cl | H | m.p. 151–152° C. |
| 3.68 | Cl | Cl | OCH$_3$ | H | m.p. 221–224° C. |
| 3.69 | Cl | Cl | OC$_2$H$_5$ | H | m.p. 184–185° C. |
| 3.70 | Cl | Cl | SCH$_3$ | H | |
| 3.71 | Cl | Cl | OC$_3$H$_7$-n | H | m.p. 135–136° C. |
| 3.72 | Cl | H | OC$_2$H$_5$ | H | |
| 3.73 | Cl | Cl | SC(CH$_3$)$_3$ | H | |
| 3.74 | Cl | Cl | OCH$_2$CF$_3$ | H | m.p. 128–130° C. |
| 3.75 | Cl | SC$_6$H$_5$ | OCH$_2$CF$_3$ | H | |
| 3.76 | Cl | SCH$_3$ | OC$_2$H$_5$ | H | |
| 3.77 | Cl | Cl | OCH$_2$CH$_2$OCH$_3$ | H | m.p. 138–140° C. |
| 3.78 | Cl | F | F | H | |
| 3.79 | Cl | F | OCH$_3$ | H | |
| 3.80 | Cl | F | SC$_2$H$_5$ | | |
| 3.81 | Cl | Cl | OCH$_2$C≡CH | H | |
| 3.82 | Cl | SCH$_3$ | Cl | Cl | m.p. 232–234° C. |
| 3.83 | Cl | SCH$_3$ | Cl | OCH$_3$ | |
| 3.84 | Cl | SCH$_3$ | Cl | SCH$_3$ | |
| 3.85 | Cl | SCH$_3$ | Cl | O—⟨C$_6$H$_4$⟩—Cl | |
| 3.86 | Cl | SCH$_3$ | Cl | —N(pyrrolidinyl) | |
| 3.87 | Cl | SCH$_3$ | Cl | OCH(CH$_3$)$_2$ | |
| 3.88 | Cl | SCH$_3$ | Cl | OCH$_2$CCl$_2$CF$_3$ | |
| 3.89 | Cl | SCH$_3$ | Cl | N(CH$_3$)C$_3$H$_7$ | |
| 3.90 | Cl | SCH$_3$ | SC$_2$H$_5$ | SC$_2$H$_5$ | |
| 3.91 | Cl | SCH$_3$ | SC$_2$H$_5$ | OCH$_3$ | |
| 3.92 | Cl | SCH$_3$ | SC$_2$H$_5$ | OCH(CH$_3$) | |
| 3.93 | Cl | Cl | CH$_3$ | Cl | |
| 3.94 | Cl | Cl | CH$_3$ | OCH$_3$ | m.p. 216–218° C. |
| 3.95 | Cl | Cl | CH$_3$ | SCH$_3$ | |
| 3.96 | Cl | Cl | CH$_3$ | N(CH$_3$)$_2$ | |
| 3.97 | Cl | SC$_2$H$_5$ | CH$_3$ | SC$_2$H$_5$ | |
| 3.98 | Cl | SC$_6$H$_5$ | CH$_3$ | SC$_6$H$_5$ | |
| 3.99 | Cl | F | CH$_3$ | F | |

TABLE 4

| No. | X | $R_1'$ | $R_2'$ | $R_3'$ | physical data |
|---|---|---|---|---|---|
| 4.1 | Cl | H | H | H | m.p. 170–173° C. |
| 4.2 | Cl | 6-CH$_3$ | H | H | m.p. 89–92° C. |
| 4.3 | Cl | 4-CH$_3$ | H | H | m.p. 170–172° C. |
| 4.4 | Cl | 5-Cl | H | H | m.p. 166–168° C. |
| 4.5 | Br | H | H | H | |
| 4.6 | Br | 5-Cl | H | H | |
| 4.7 | Br | 4-CH$_3$ | H | H | |
| 4.8 | Br | 6-CH$_3$ | H | H | |
| 4.9 | F | H | H | H | |
| 4.10 | Cl | 5-CH$_3$ | H | H | |
| 4.11 | Cl | 5-Br | H | H | |
| 4.12 | Cl | 3-Br | 5-Br | H | |

TABLE 4-continued

| No. | X | R$_1'$ | R$_2'$ | R$_3'$ | physical data |
|---|---|---|---|---|---|
| 4.13 | Cl | 3-Cl | 5-Cl | H | |
| 4.14 | Cl | 4-CH$_3$ | 6-CH$_3$ | H | |
| 4.15 | Cl | 3-NO$_2$ | H | H | |
| 4.16 | Cl | 5-NO$_2$ | H | H | |
| 4.17 | Cl | 3-C$_4$H$_9$(tert.) | H | H | |
| 4.18 | Cl | 4-C$_2$H$_5$ | H | H | |
| 4.19 | Cl | 3-CH$_3$ | 4-CH$_3$ | H | |
| 4.20 | Cl | 3-CH$_3$ | 5-CH$_3$ | H | |
| 4.21 | Cl | 3-C$_2$H$_5$ | 6-CH$_3$ | H | |
| 4.22 | Cl | 6-Br | H | H | |
| 4.23 | Cl | 3-Cl | 5-CF$_3$ | H | m.p. 178–179° C. |
| 4.24 | Cl | 3-CH$_3$ | 5-Br | H | |
| 4.25 | Cl | 4-CH$_3$ | 6-Br | H | |
| 4.26 | Cl | 4-Cl | 6-CH$_3$ | H | |
| 4.27 | Cl | 3-NO$_2$ | 6-CH$_3$ | 6Me | |
| 4.28 | Cl | 3-NO$_2$ | 4-Cl | H | |
| 4.29 | Cl | 3-NO$_2$ | 5-Cl | H | |
| 4.30 | Cl | 3-OCH$_3$ | H | H | |
| 4.31 | Cl | 3-OC$_2$H$_5$ | H | H | |
| 4.32 | Cl | 6-OC$_2$H$_5$ | H | H | |
| 4.33 | Br | 3-NO$_2$ | H | H | |
| 4.34 | Br | 5-NO$_2$ | H | H | |
| 4.35 | Br | 4-CH$_3$ | 6-CH$_3$ | H | |
| 4.36 | Cl | 6-CH$_3$ | H | H | |
| 4.37 | Br | 6-CH$_3$ | H | H | |
| 4.38 | Cl | 5-CF$_3$ | H | H | |
| 4.39 | Cl | 3-Br | 5-Cl | H | m.p. 163–164° C. |
| 4.40 | Cl | 3-COOC$_2$H$_5$ | 5-Br | H | m.p. 219–220° C. |

TABLE 5

| No. | X | R$_1'$ | R$_2'$ | physical data |
|---|---|---|---|---|
| 5.1 | Cl | H | H | m.p. 155–157° C. |
| 5.2 | Cl | 2-Cl | H | |
| 5.3 | Cl | 2-Cl | 6-Cl | |
| 5.4 | Cl | 2-OCH$_3$ | 6-OCH$_3$ | |
| 5.5 | Cl | 2-CH$_3$ | H | |
| 5.6 | Cl | 4-CH$_3$ | H | |
| 5.7 | Cl | 5-CH$_3$ | H | |
| 5.8 | Cl | 6-CH$_3$ | H | |
| 5.9 | Cl | 2-F | H | |
| 5.10 | Cl | 5-Br | H | |
| 5.11 | Cl | 4-Cl | 6-Cl | |
| 5.12 | Cl | 4-NO$_2$ | H | |
| 5.13 | Br | H | H | |
| 5.14 | Br | 2-Cl | H | |
| 5.15 | F | H | H | |
| 5.16 | J | H | H | |

TABLE 6

| No. | X | R$_1'$ | R$_2'$ | physical data |
|---|---|---|---|---|
| 6.1 | Cl | H | H | m.p. 227–228° C. |
| 6.2 | Cl | 2-CH$_3$ | H | |
| 6.3 | Cl | 3-CH$_3$ | H | |
| 6.4 | Cl | 3-C$_3$H$_7$(iso) | H | |
| 6.5 | Cl | 2-C$_4$H$_9$(tert.) | H | |
| 6.6 | Cl | 2-Cl | H | |
| 6.7 | Cl | 2-Br | H | |
| 6.8 | Cl | 2-J | H | |
| 6.9 | Cl | 3-Cl | H | |
| 6.10 | Cl | 3-Br | H | |
| 6.11 | Cl | 3-F | H | |
| 6.12 | Cl | 2-OCH$_3$ | H | |
| 6.13 | Cl | 2-CH$_3$ | 6-Cl | |
| 6.14 | Cl | 2-CH$_3$ | 5-NO$_2$ | |
| 6.15 | Cl | 2-Cl | 3-NO$_2$ | |
| 6.16 | Cl | 2-Cl | 4-NO$_2$ | |
| 6.17 | Cl | 3-Cl | 5-NO$_2$ | |
| 6.18 | Br | H | H | |
| 6.19 | Br | 2-CH$_3$ | H | |
| 6.20 | Br | 2-Cl | H | |
| 6.21 | Br | 3-F | H | |

TABLE 7

| No. | X | R$_1'$ | R$_2'$ | physical data |
|---|---|---|---|---|
| 7.1 | Cl | H | H | m.p. >250° C. |
| 7.2 | Cl | 6-Cl | H | |
| 7.3 | Cl | 4-CH$_3$ | 6-Cl | |
| 7.4 | Cl | 5-CH$_3$ | H | |
| 7.5 | Cl | 5-CH$_3$ | H | |
| 7.6 | Br | H | H | |
| 7.7 | Br | 6-Cl | H | |
| 7.8 | Br | 6-CH$_3$ | H | |
| 7.9 | Cl | 6-CH$_3$ | H | |
| 7.10 | Cl | 6-SCH$_3$ | H | |
| 7.11 | Cl | 6-OCH$_3$ | H | |
| 7.12 | Cl | 6-SC$_2$H$_5$ | H | |
| 7.13 | F | H | H | |
| 7.14 | F | 6-Cl | H | |
| 7.15 | J | H | H | |

TABLE 8

| No. | X | R$_1'$ | R$_2'$ | physical data |
|---|---|---|---|---|
| 8.1 | Cl | H | H | |
| 8.2 | Br | H | H | |
| 8.3 | F | H | H | |
| 8.4 | Cl | 3-Cl | 5-Cl | |
| 8.5 | Cl | 3-Cl | 6-Cl | |
| 8.6 | Cl | 3-CH$_3$ | H | |
| 8.7 | Cl | 3-Cl | H | |

TABLE 8-continued

| No. | X | R₁' | R₂' | physical data |
|---|---|---|---|---|
| 8.8 | Cl | 3-OCH₃ | 6-CH₃ | |
| 8.9 | Cl | 3-Cl | 6-CH₃ | |
| 8.10 | Cl | 3-OCH₃ | 6-OCH₃ | |
| 8.11 | Cl | 6-CH₃ | H | |
| 8.12 | Cl | 6-Cl | H | |
| 8.13 | Br | 3-Cl | 5-Cl | |
| 8.14 | Br | 3-Cl | 6-Cl | |
| 8.15 | Br | 3-OCH₃ | 6-OCH₃ | |

TABLE 9

| No. | X | R₁' | R₂' | physical data |
|---|---|---|---|---|
| 9.1 | Cl | H | H | |
| 9.2 | Br | H | H | |
| 9.3 | Cl | 3-CH₃ | H | |
| 9.4 | Cl | 5-CH₃ | H | |
| 9.5 | Cl | 3-C₂H₅ | H | |
| 9.6 | Cl | 3-C₂H₅ | 5-CH₃ | |
| 9.7 | Cl | 3-CH₃ | 6-CH₃ | |
| 9.8 | Cl | 6-C₃H₉(sec.) | H | |
| 9.9 | Cl | 5-CH₃ | 6-CH₃ | |
| 9.10 | Br | 3-CH₃ | H | |
| 9.11 | Cl | 3-Br | H | |
| 9.12 | Cl | 5-Br | H | |
| 9.13 | Cl | 3-Cl | 5-Cl | |
| 9.14 | Cl | 5-Br | 3-Cl | |
| 9.15 | Cl | 3-Cl | H | |
| 9.16 | Cl | 5-Cl | H | |
| 9.17 | Cl | 3-Cl | 5-CH₃ | |
| 9.18 | F | H | H | |
| 9.19 | J | H | H | |

TABLE 10

| No. | X | Y₁ | Y₂ | physical data |
|---|---|---|---|---|
| 10.1 | Cl | N | N | m.p. 110–113° C. |
| 10.2 | Cl | CH | N | m.p. 148–151° C. |
| 10.3 | Br | N | N | |
| 10.4 | Br | CH | N | |
| 10.5 | J | N | N | |
| 10.6 | F | N | N | |
| 10.7 | F | CH | N | |
| 10.8 | Cl | CH | CH | |
| 10.9 | Br | CH | CH | |
| 10.10 | Cl | N | CH | |
| 10.11 | Br | N | CH | |

2. Formulation Examples for Liquid Active Ingredients of Formula I (throughout, percentages are by weight)

| 2.1. Emulsifiable concentrates | (a) | (b) | (c) |
|---|---|---|---|
| a compound from the Tables | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2.2. Solutions | (a) | (b) | (c) | (d) |
|---|---|---|---|---|
| a compound from the Tables | 80% | 10% | 5% | 95% |
| ethylene glycol monomethyl ether | 20% | — | — | — |
| polyethylene glycol (MW 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

(MW = molecular weight)

These solutions are suitable for application in the form of micro-drops.

| 2.3. Granulates | (a) | (b) |
|---|---|---|
| a compound from the Tables | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | (a) | (b) |
|---|---|---|
| a compound from the Tables | 2% | 5% |
| highly dispersed silicic acid | 1% | 5% |
| talcum | 97% | — |
| kaolin | — | 90% |

Ready-for-use dusts are obtained by homogeneously mixing the carriers with the active ingredient.

Formulation Examples for Solid Active Ingredients of Formula I (throughout, percentages are by weight)

| 2.5. Wettable powders | (a) | (b) | (c) |
|---|---|---|---|
| a compound from the Tables | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is homogeneously ground in a suitable mill, affording wettable powders which can be diluted with water to give suspensions of the desired concentration.

| 2.6 Emulsifiable concentrate | |
|---|---|
| a compound from the Tables | 10% |
| octylphenol polyethylene glycol ether (4-5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 2.7. Dusts | (a) | (b) |
|---|---|---|
| a compound from the Tables | 5% | 8% |
| talcum | 95% | — |
| kaolin | — | 92% |

Ready-for-use dusts are obtained by mixing the active ingredients with the carriers and grinding the mixture in a suitable mill.

| 2.8. Extruder granulate | |
|---|---|
| a compound from the Tables | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| 2.9. Coated granulate | |
|---|---|
| a compound from the Tables | 3% |
| polyethylene glycol (MW 200) | 3% |
| kaolin | 94% |

(MW = molecular weight)

The finely ground active ingredient is uniformly applied, in a mixer, to the kaolin moistened with polyethylene glycol. Non-dusty coated granulates are obtained in this manner.

| 2.10. Suspension concentrate | |
|---|---|
| a compound from the Tables | 40% |
| ethylene glycol | 10% |
| nonylphenol polyethylene glycol ether (15 moles of ethylene oxide) | 6% |
| sodium lignosulfonate | 10% |
| carboxymethylcellouse | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

BIOLOGICAL EXAMPLES

Example 3.1: Action Against *Colletotrichum lagenarium* on *Cucumis sativus* L.

(a) After 2 weeks' cultivation, cucumber plants are sprayed with a spray mixture prepared from a wettable powder formulation of the test compound (concentration: 200 ppm).

After 48 hours the plants are infected with a spore suspension ($1.5 \times 10^5$ spores/ml) of the fungus and incubated for 36 hours at high humidity and a temperature of 23° C. Incubation is then continued at normal humidity and at from 22° C. to 23° C.

The protective action is assessed on the basis of the fungal attack 7 to 8 days after infection.

(b) After 2 weeks' cultivation, cucumber plants are treated by soil application with a spray mixture prepared from a wettable powder formulation of the test compound (concentration: 60 or 20 ppm based on the volume of soil).

After 48 hours the plants are infected with a spore suspension ($1.5 \times 10^5$ spores/ml) of the fungus and incubated for 36 hours at high humidity and a temperature of 23° C. Incubation is then continued at normal humidity and at 22° C.

The protective action is assessed on the basis of the fungal attack 7 to 8 days after infection.

(c) After 2 weeks' cultivation, cucumber plants are treated with a spray mixture prepared from a wettable powder formulation of the test compound (concentration: 200 ppm).

After 3 weeks the plants are infected with a spore suspension ($1.5 \times 10^5$ spores/ml) of the fungus and incubated for 36 hours at high humidity and a temperature of 23° C. Incubation is then continued at normal humidity and at from 22° to 23° C.

The protective action is assessed on the basis of the fungal attack 7 to 8 days after infection.

Compounds from Tables 1 to 10 exhibited good activity in tests (a) and (b). For example, compounds 1.1, 1.2, 1.5, 1.6, 1.9, 1.18, 1.35, 1.55, 1.56, 1.60, 1.63, 1.64, 1.71, 1.73, 1.80, 1.85, 1.96, 1.100, 1.114, 1.149, 1.156, 2.6, 2.7, 2.18, 2.27, 2.31, 2.36, 2.39, 2.49, 2.56, 3.1, 3.7, 3.19, 3.33, 3.40, 3.77, 3.94, 4.1, 4.2, 4.3, 6.1, 7.1, 10.1 and 10.2 confined fungal attack to 0 to 20%. On the other hand, Colletotrichum attack was 100% on untreated and infected control plants.

Example 3.2: Action Against *Puccinia graminis* on Wheat (a) Wheat plants are sprayed 6 days after sowing with a spray mixture (0.02% active ingredient) prepared from a wettable powder formulation of the test compound. After 24 hours the treated plants are infected with a uredospore suspension of the fungus. The infected plants are incubated for 48 hours at 95-100% relative humidity and about 20° C. and then stood in a greenhouse at about 22° C. Evaluation of rust pustule development is made 12 days after infection.

(b) 5 days after sowing, wheat plants are watered with a spray mixture (0.006% active ingredient based on the volume of soil) prepared from a wettable powder formulation of the test compound. After 48 hours the treated plants are infected with a uredospore suspension of the fungus. The infected plants are incubated for 48 hours at 95-100% relative humidity and about 20° C. and then stood in a greenhouse at about 22° C. Evaluation of rust pustule development is made 12 days after infection.

Compounds from Tables 1 to 10 exhibited good activity against *Puccinia fungi*. For example, compounds 1.1, 1.3, 1.4, 1.9, 1.56, 1.60, 1.63, 1.71, 1.79, 1.80, 1.85, 1.92, 1.100, 1.112, 2.1, 2.39, 2.49, 3.7, 3.94, 4.1, 6.1, 7.1 and 10.2 confined Puccinia attack to 0 to 20%. On the other hand, Puccinia attack was 100% on untreated and infected control plants.

Example 3.3: Action Against *Phytophthora infestans* on Tomato Plants (a) After 3 weeks' cultivation, tomato plants are sprayed with a spray mixture (0.02% active ingredient) prepared from a wettable powder formulation of the test compound. After 24 hours the treated plants are infected with a sporangia suspension of the fungus. The fungal attack was evaluated after incubating the infected plants for 5 days at 90-100% relative humidity and 20° C.

(b) After a cultivation period of 3 weeks tomato plants are watered with a spray mixture (0.006% active ingredient based on the volume of soil) prepared from a wettable powder formulation of the test compound. Care is taken that the spray mixture does not come into contact with the parts of the plants that are above the soil. After 48 hours the treated plants are infected with a sporangia suspension of the fungus. The fungal attack is evaluated after incubating the infected plants for 5 days at 90-100% relative humidity and 20° C.

Compounds from Tables 1 to 10 exhibited a good protective action against the Phytophthora fungus. For example, compounds 1.1, 1.4, 1.6, 1.7, 1.35, 1.74, 1.75, 1.89, 1.96, 2.6, 2.39, 2.49, 3.38, 3.74, 3.77, 5.1 and 7.1 confined fungal attack to 0 to 20%. On the other hand, Phytophthora attack was 100% on untreated and infected control plants.

Example 3.4: Action Against *Cercospora arachidicola* in Groundnut Plants

Groundnut plants 10-15 cm in height are sprayed with a spray mixture (0.02% active ingredient) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks appear.

Evaluation of the fungicidal action is effected 12 days after infection based on the number and size of the specks.

Compared with untreated and infected control plants (number and size of the specks=100%), Cercospora attack on groundnut plants that had been treated with compounds from Tables 1 to 10, for example compounds 1.3, 1.41, 1.57, 1.112, 1.114, 2.31 and 2.39, was reduced to 10-20%.

Example 3.5: Action Against *Plasmopara viticola* on Vines (a) Vine seedlings at the 4 to 5 leaf stage are sprayed with a spray mixture (0.02% active ingredient) prepared from a wettable powder formulation of the test compound. After 24 hours the treated plants are infected with a sporangia suspension of the fungus. Fungal attack is evaluated after incubation for 6 days at 95-100% relative humidity and 20° C.

(b) Vine seedlings at the 4 to 5 leaf stage are infected with a sporangia suspension of the fungus. After having been incubated for 24 hours in a humidity chamber at 95-100% relative humidity and 20° C., the infected plants are dried and sprayed with a spray mixture (0.06% active ingredient) prepared from a wettable powder formulation of the test compound. After the spray coating has dried the treated plants are placed in the humidity chamber again. The fungal attack is evaluated 6 days after infection.

Compounds from Tables 1 to 10, for example 1.5, 1.6, 1.18 and 1.56, exhibited a good protective action against *Plasmopara viticola* (0-20% attack). On the other hand, Plasmopara attack was 100% on untreated and infected control plants.

Example 3.6: Action Against *Pyricularia oryzae* on Rice Plants (a) After 2 weeks' cultivation, rice plants are sprayed wich a spray mixture (0.02% active ingredient) prepared from a wettable powder formulation of the test compound. After 48 hours, the treated plants are infected with a conidia suspension of the fungus. Evaluation of fungal attack is made after incubation for 5 days at 95-100% relative humidity and 24° C.

(b) 2 week-old rice plants are watered with a spray mixture (0.006% active ingredient based on the volume of soil) prepared from a wettable powder formulation of the test compound. The pots are then filled with water until the lowest parts of the stalks of the rice plants stand in water. After 96 hours the treated rice plants are infected with a conidia suspension of the fungus. Evaluation of fungal attack is made after incubation of the infected plants for 5 days at 95-100% relative humidity and approximately 24° C.

Rice plants that had been treated with a spray mixture containing one of the compounds from Tables 1 to 10 as active ingredient exhibited only slight fungal attack compared with untreated control plants (100% attack).

For example in test (a) compounds 1.2, 1.7, 1.9, 1.20, 1.27, 1.35, 1.55, 1.57, 1.58, 1.63, 1.79, 1.80, 1.83, 1.85, 1.92, 1.94, 1.129, 2.18, 2.36, 2.39, 2.49, 3.2, 3.33, 3.35, 3.38, 3.40, 3.49, 3.67, 3.71, 3.74, 3.94, and in test (b) compounds 1.2, 1.35, 1.55, 1.58, 1.60, 1.63, 1.92, 1.100, 1.120, 1.129, 1.156 and 3.17, confined fungal attack to 0 to 20%.

Example 3.7: Action Against *Pseudomonas tomato* on Tomato Plants (a) After 3 weeks' cultivation tomato plants are treated by foliar application with a spray mixture prepared from a wettable powder formulation of the test compound (concentration: 200 ppm). After 3.5 weeks the plants are inoculated with a bacterial suspension (108 bacteria/ml) and incubated for 6 days at high humidity and at a temperature of 25° C. The protective action is evaluated 7 to 8 days after inoculation on the basis of the bacterial attack.

(b) After 3 weeks' cultivation tomato plants are treated by soil application with a spray mixture prepared from a wettable powder formulation of the test compound (concentration: 60 ppm based on the volume of soil). After 3.5 weeks the plants are inoculated with a bacterial suspension (108 bacteria/ml) and incubated for 6 days at high humidity and at a temperature of 25° C.

The protective action is evaluated 7 to 8 days after inoculation on the basis of the bacterial attack.

Compounds from Tables 1 to 10 exhibited a good protective action against Pseudomonas. For example in test (a) compounds 1.1, 1.6, 1.60, 1.63, 1.73, 1.94, 1.100, 1.112, 1.114, 2.1, 2.27, 2.31, 3.33, and in test (b) compounds 1.1, 1.4, 1.6, 1.7, 1.8, 1.35, 1.57, 1.58, 1.60, 1.63, 1.73, 1.74, 1.75, 1.79, 1.85, 1.89, 1.92, 1.94, 1.100, 2.7, 2.31, 2.39, 2.56, 3.1, 3.33 and 3.94 confined bacterial attack to 0 to 20%. On the other hand, Pseudomonas attack was 100% on untreated and infected control plants.

Example 3.8: Action Against Tobacco Mosaic Virus on Tobacco 8-week-old tobacco plants are sprayed (concentration: 200 ppm) or injected (concentration: 200 ppm) with a formulated solution of the test compound. After 4 days the plants are mechanically inoculated with a suspension of Tobacco Mosaic Virus (0.5 μg/ml+carborundum) and incubated at a temperature of 20°-22° C.

The protective action is evaluated 7 days after inoculation on the basis of the number and size of the local lesions.

Compounds from Tables 1 to 10 exhibited a good protective action against Tobacco Mosaic Virus. Lesions of 100% were, however, observed on untreated and infected control plants.

Example 3.9: Action Against *Pseudomonas lachrymans* on *Cucumis sativus* L.

(a) After 2 weeks' cultivation, cucumber plants are sprayed with a spray mixture prepared from a wettable powder formulation of the test compound (concentration: 20 ppm).

After 1 week, the plants are infected with a bacterial suspension ($10^8$ bacteria/ml) and incubated for 7 days at high humidity and a temperature of 23° C.

The protective action is evaluated 7 to 8 days after infection on the basis of the bacterial attack.

(b) After 2 weeks' cultivation cucumber plants are treated by soil application with a spray mixture prepared from a wettable powder formulation of the test compound (concentrations: 60, 20, 6, 2 ppm based on the volume of soil).

After 1 week the plants are infected with a bacterial suspension ($10^8$ bacteria/ml) and incubated for 7 days at high humidity and a temperature of 23° C.

The protective action is evaluated 7 to 8 days after infection on the basis of the bacterial attack.

Compounds from Tables 1 to 10 exhibited a good protective action against Pseudomonas attack. For example bacterial attack was confined to 0 to 20% in test (a) by compounds 1.18, 1.35, 1.85, 1.103, 2.7, 2.30, 2.31, 4.1, 6.1 and in test (b) by compounds 1.18, 2.7, 2.31, 2.36 and 2.85. On the other hand, Pseudomonas attack was 100% on untreated and infected control plants.

Example 3.10: Action Against *Xanthomonas oryzae* on Rice (*Oryza sativa*)

(a) After 3 weeks' cultivation in a greenhouse, rice plants of the variety "Calora" or "S6" are sprayed with the test substance in the form of a spray mixture (0.02% active ingredient). After this spray coating has dried for 1 day the plants are placed in a climatic chamber at 24° C. and 75-85% relative humidity and infected. The infection is carried out by cutting off the leaf tips with shears that have beforehand been immersed in a suspension of *Xanthomonas oryzae*. After an incubation period of 10 days the cut leaves that have been attacked become shrivelled, roll up and become necrotic. The residual activity of the test substance is evaluated on the basis of the extent of these disease symptoms.

(b) After a cultivation period of 3 weeks in a greenhouse, rice plants of the variety "Calora" or "S6" are watered with a suspension of the test substance (0.006% active ingredient based on the volume of soil). Three days after this treatment the plants are placed in a climatic chamber at 24° C. and 75-85% relative humidity and infected. The infection is carried out by cutting off the leaf tips with shears that have beforehand been immersed in a suspension of *Xanthomonas oryzae*. After an incubation period of 10 days the cut leaves that have been attacked become shrivelled, roll up and become necrotic. The systemic activity of the test substance is evaluated on the basis of the extent of these disease symptoms.

Compounds from Tables 1 to 10 exhibited a good protective action against *Xanthomonas oryzae*. For example in test (a) compounds 1.3, 1.4, 1.5, 1.8, 1.9, 1.56, 1.58, 1.59, 1.60, 1.63, 1.64, 1.92, 1.100, 1.114, 1.120, 1.129, 2.1, 2.27, 2.31, 3.19, 3.33 and 3.34 and in test (b) compounds 1.3, 1.6, 1.8, 1.9, 1.55, 1.56, 1.57, 1.58, 1.59, 1.60, 1.63, 1.85, 1.92, 1.94, 1.100, 1.129, 1.149, 2.1, 2.27, 2.39, 2.49 and 3.17 confined the bacterial attack to 0 to 20%. On the other hand, disease attack was 100% on untreated and infected control plants.

Example 3.11: Action Against *Xanthomonas vesicatoria* on Paprika (*Capsicum annuum*)

(a) After 3 weeks' cultivation in a greenhouse, paprika plants of the variety "California Wonder" are sprayed with the test substance in the form of a spray mixture (0.02% active ingredient). After the spray coating has dried for one day, the plants are placed in a climatic chamber at 26° C. and 95-100% relative humidity and infected by spraying the undersides of the leaves with a standardised suspension of *Xanthomonas vesicatoria*. After an incubation period of 6 days, round, initially watery, later necrotic, light specks form on the leaves attacked. The residual activity of the test substance is evaluated on the basis of the extent of these flecks.

b) After a cultivation period of 3 weeks in a greenhouse, paprika plants of the variety "California Wonder" are watered with a suspension of the test substance (0.006% active ingredient based on the volume of soil) Three days after this treatment the plants are placed in a climatic chamber at 26° C. and 95-100% relative humidity and infected by spraying the undersides of the leaves with a standardised suspension of *Xanthomonas vesicatoria*. After an incubation period of 6 days, round, initially watery, later necrotic, light specks form on the leaves attacked. The systemic activity of the test substance is evaluated on the basis of the extent of these flecks.

Compounds from Tables 1 to 10 exhibited a good protective action against *Xanthomonas vesicatoria*. For example in test (a) compounds 1.1, 1.57, 1.58, 1.85, 1.89, 1.112, 2.21, 2.31, 3.5, 3.19, 3.27, 3.7 and 3.9 and in test (b) compounds 1.1, 1.4, 1.6, 1.7, 1.9, 1.35, 1.41, 1.74, 1.75, 1.79, 1.85, 1.89, 1.103, 1.112, 1.129, 2.21, 2.31, 2.56, 3.1, 3.34, 3.7 and 3.9 confined the bacterial attack to 0 to 20%. On the other hand, disease attack was 100% on untreated and infected control plants.

Example 3.12: Dressing Action Against *Fusarium nivale* in Rye

Rye seeds of the variety Tetrahell naturally infected with *Fusarium nivale* are dressed with the test substance on a mixer roll, the following concentrations being used: 600, 200 or 60 ppm a.i. (based on the weight of the seed).

The infected and treated rye is sown in October in the open with a seeder in plots 3 meters long containing 6 rows. Three replicates are carried out with each test compound.

Until the attack is evaluated, the test plants are cultivated under normal field conditions (preferably in a region with unbroken snow cover during the winter months).

To determine the effectiveness of the test compounds, the percentage of plants attacked by Fusarium is assessed in Spring directly after the snow has melted.

Compounds from Tables 1 to 10 exhibited a good protective action against Fusarium. Disease attack on untreated and infected control plants was 100%.

Example 3.13: Dressing Action Against *Helminthosporium gramineum* on Barley

Winter barley seeds of the variety "C1" naturally infected with *Helminthosporium gramineum* are dressed with the test substance on a mixer roll, the following concentrations being used: 600, 200 or 60 ppm a.i. (based on the weight of the seed).

The infected and treated barley is sown in October in the open with a seeder in plots 2 meters long containing 3 rows. Three replicates are carried out with each test compound.

Until the attack is evaluated, the test plants are cultivated under normal field conditions.

To determine the effectiveness of the test compounds, the percentage of stalks attacked by Helminthosporium is assessed at the time of ear emergence.

Compounds from Tables 1 to 10 exhibited a good protective action against Helminthospora. On the other hand, disease attack was 100% on untreated and infected control plants.

Example 3.14 Dressing Action Against *Ustilago nuda* on Barley

Winter barley seeds of the variety "RM1" naturally infected with *Ustilago nuda* are dressed with the test substance on a mixer roll, the following concentrations being used: 600, 200 or 60 ppm a.i. (based on the weight of the seed).

The infected and treated barley is sown in October in the open with a seeder in plots 2 meters long containing 3 rows. Three replicates are carried out with each test compound.

Until the attack is evaluated, the test plants are cultivated under normal field conditions.

To determine the effectiveness of the test compounds, the percentage of ears attacked by Ustilago is assessed when the plants are in bloom.

Compounds from Tables 1 to 10 exhibited a good protective action against Ustilago. On the other hand, disease attack was 100% on untreated and infected control plants.

Example 3.15: Dressing Action Against *Colletotrichum lagenarium* on *Cucumis sativus* L.

Cucumber seeds are dressed with a solution of the active ingredient (concentration: 180 g/100 kg of seed). The seeds are sown. After 4 weeks the plants are infected with a spore suspension ($1.5 \times 10^5$ spores/ml) of the fungus and incubated for 36 hours at high humidity and a temperature of 23° C. The incubation is then continued at normal humidity and at from 22° to 23° C. The protective action is evaluated on the basis of the fungal attack 7 to 8 days after infection.

Compounds from Tables 1 to 10 exhibited a good protective action against Colletotrichum. Fungal attack was 100% on infected control plants, where the seeds had not been treated.

Example 3.16: Residual-Protective Action Against *Venturia inaequalis* on Apple Shoots Apple cuttings with 10–20 cm long fresh shoots are sprayed with a spray mixture (0.02% active ingredient) prepared from a wettable powder formulation of the test compound. The treated plants are infected 24 hours later with a conidia suspension of the fungus. The plants are then incubated for 5 days at 90–100% relative humidity and stood in a greenhouse for a further 10 days at 20°–24° C. Scab attack was evaluated 15 days after infection.

Compounds from Tables 1 to 10 exhibited a good protective action against Venturia. For example compound 1.114 confined scab attack to 5 to 20%. On the other hand, Venturia attack was 100% on untreated and infected shoots.

Example 3.17: Action Against *Erysiphe graminis* on Barley (a) Barley plants about 8 cm in height are sprayed with a spray mixture (0.02% active ingredient) prepared from a wettable powder formulation of the test compound. 3 to 4 hours later the treated plants are dusted with conidia of the fungus. The infected barley plants are stood in a greenhouse at about 22° C. and the fungal attack is evaluated after 10 days.

(b) Barley plants about 8 cm in height are watered with a spray mixture (0.006% active ingredient, based on the volume of soil) prepared from a wettable powder formulation of the test compound. Care is taken that the spray mixture does not come into contact with the parts of the plants above the soil.

The treated plants are infected 48 hours later with conidia of the fungus. The infected barley plants are stood in a greenhouse at about 22° C. and evaluation of fungal attack is made after 10 days.

Compounds from Tables 1 to 10, for example compounds 1.1, 1.2, 1.5, 1.7, 1.9, 1.18, 1.20, 1.27,. 1.35, 1.41, 1.53, 1.56, 1.63, 1.64, 1.67, 1.79, 1.80, 1.85, 1.89, 1.94, 1.100, 1.103, 1.120, 1.149, 2.18, 2.36, 3.71, 4.1, 4.2, 10.1 and 10.2 confined fungal attack to less than 20%, whilst attack on untreated and infected control plants was 100%.

What is claimed is:

1. A compound of formula I

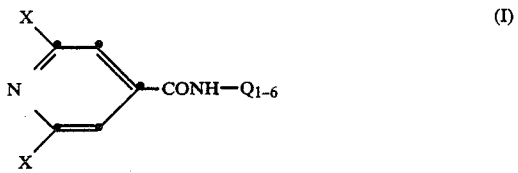

in which
X in ortho/ortho'-position are equal and represent fluorine, chlorine, bromine or iodine;
$Q_1$ is unsubstituted pyrimidin-4-yl, or pyrimidin-4-yl substituted by $R_1$, $R_2$, and $R_3$;
$Q_2$ is unsubstituted pyrimidin-2-yl, or pyrimidin-2-yl substituted by $R_1$, $R_2$ and $R_3$;
$Q_3$ is unsubstituted pyrimidin-5-yl, or pyrimidin-5-yl substituted by $R_1$, $R_2$ and $R_3$;

$Q_4$ is pyridin-2-yl, pyridin-3-yl or pyridin-4-yl each of which is unsubstituted or substituted by $R_1$, $R_2$ and $R_3$;

$Q_5$ is pyridazin-3-yl or pyridazin-4-yl each of which is unsubstituted or substituted by $R_1$, $R_2$ and $R_3$;

$Q_6$ is unsubstituted pyrazin-2-yl, or pyrazin-2-yl substituted by $R_1$, $R_2$ and $R_3$;

$R_1$, $R_2$, $R_3$ are hydrogen, halogen, $C_1$–$C_6$alkyl, $C_1$–$C_6$haloalkyl having from 1 to 3 halogen atoms, $C_1$–$C_6$alkoxy, $C_2$–$C_6$alkoxyalkyl, $C_1$–$C_6$thioalkyl, $C_1$–$C_6$haloalkoxy having from 1 to 5 halogen atoms, $C_3$–$C_6$alkenyloxy, $C_3$–$C_6$alkynyloxy, $C_3$–$C_6$thioalkenyl, $C_3$–$C_6$cycloalkyl, $C_3$–$C_6$cycloalkyl substituted by methyl, or nitro, cyano, the radical $CH(OR_4)_2$ or $COOR_4$ in which $R_4$ is $C_1$–$C_4$alkyl; $R_1$, $R_2$, $R_3$ are also phenyl, phenoxy, thiophenyl, benzyl, benzyloxy or thiobenzyl; or phenyl, phenoxy, thiophenyl, benzyl, benzyloxy or thiobenzyl each substituted at least once by $C_1$–$C_3$alkyl, $C_1$–$C_3$alkoxy, $C_1$–$C_3$haloalkyl having from 1 to 3 halogen atoms, halogen, nitro or by cyano; and $R_1$, $R_2$, $R_3$ are also $N(R_5)R_6$ in which $R_5$ and $R_6$, independently of one another, are each $C_1$–$C_6$alkyl;

$R_1$, $R_2$ and $R_3$ are also piperidinyl, pyrrolidinyl, morpholinyl, imidazolyl or triazolyl, or piperidinyl, pyrrolidinyl, morpholinyl, imidazolyl, or triazolyl each substituted by $C_1$–$C_3$alkyl, $C_1$–$C_3$-alkoxy, $C_1$–$C_3$haloalkyl having from 1 to 3 halogen atoms, halogen, nitro or by cyano.

2. A compounds of formula I according to claim 1, in which $Q_1$ is pyrimidin-4-yl substituted by $R_1$, $R_2$ and $R_3$, and X, $R_1$, $R_2$ and $R_3$ are as defined for formula I.

3. A compounds of formula I according to claim 2, in which X is chlorine, $Q_1$ is pyrimidin-4-yl and $R_1$, $R_2$ and $R_3$ in the 2-, 5- and 6-positions are hydrogen, fluorine, chlorine, bromine, $C_1$–$C_4$alkyl, $C_1$–$C_2$haloalkyl having from 1 to 3 fluorine or chlorine atoms, $C_1$–$C_3$alkoxy, $C_2$–$C_4$alkoxyalkyl, $C_1$–$C_4$thioalkyl, $C_1$–$C_2$haloalkoxy having from 1 to 3 fluorine or chlorine atoms, $C_3$–$C_4$alkenyloxy, $C_3$–$C_4$alkynyloxy, cyclopropyl, nitro, cyano or $COOR_4$ in which $R_4$ is $C_1$–$C_4$alkyl; and $R_1$, $R_2$ and $R_3$ are also phenyl, phenoxy, thiophenyl, benzyl, dimethylamino.

4. A compound selected from:
N-(2-cyclopropyl-5-ethyl-6-chloropyrimidin-4-yl)-2,6-dichloroisonicotinic acid amide;
N-(2-cyclopropyl-5-methyl-6-chloropyrimidin-4-yl)-2,6-dichloroisonicotinic acid amide;
N-(2,5-dimethyl-6-chloropyrimidin-4-yl)-2,6-dichloroisonicotinic acid amide;
N-(2,5-diethyl-6-chloropyrimidin-4-yl)-2,6-dichloroisonicotinic acid amide;
N-(2-chloro-6-thiomethylpyrimidin-4-yl)-2,6-dichloroisonicotinic acid amide;
N-(2-methoxy-5-chloropyrimidin-4-yl)-2,6-dichloroisonicotinic acid amide;
N-(2,5-dichloropyrimidin-4-yl)-2,6-dichloroisonicotinic acid amide;
N-(2,6-dimethylpyrimidin-4-yl)-2,6-dichloroisonicotinic acid amide;
N-(5-methyl-6-chloropyrimidin-4-yl)-2,6-dichloroisonicotinic acid amide;
N-(5-n-propyl-6-chloropyrimidin-4-yl)-2,6-dichloroisonicotinic acid amide;
N-(5-ethyl-6-chloropyrimidin-4-yl)-2,6-dichloroisonicotinic acid amide;
N-(2,5,6-trichloropyrimidin-4-yl)-2,6-dichloroisonicotinic acid amide;
N-(2-dimethylamino-6-methoxypyrimidin-4-yl)-2,6-dichloroisonicotinic acid amide;
N-(2-ethyl-5-methyl-6-chloropyrimidin-4-yl)-2,6-dichloroisonicotinic acid amide;
N-(2-trifluoromethoxy-5-chloropyrimidin-4-yl)-2,6-dichloroisonicotinic acid amide;
N-(2-methoxy-5-fluoropyrimidin-4-yl)-2,6-dichloroisonicotinic acid amide;
N-(2-chloro-5-fluoropyrimidin-4-yl)-2,6-dichloroisonicotinic acid amide;
N-(2-isopropoxy-5-chloropyrimidin-4-yl)-2,6-dichloroisonicotinic acid amide;
N-(2-isopropyl-6-chloropyrimidin-4-yl)-2,6-dichloroisonicotinic acid amide;
N-(2-chloro-6-n-propylpyrimidin-4-yl)-2,6-dichloroisonicotinic acid amide;
N-(2-n-propoxy-5-chloropyrimidin-4-yl)-2,6-dichloroisonicotinic acid amide;
N-(2-isopropyl-6-ethylthiopyrimidin-4-yl)-2,6-dichloroisonicotinic acid amide;
N-(2-isopropyl-6-isopropylthiopyrimidin-4-yl)-2,6-dichloroisonicotinic acid amide;
N-(2-chloro-6-methylpyrimidin-4-yl)-2,6-dichloroisonicotinic acid amide;
N-pyridin-2-yl-2,6-dichloroisonicotinic acid amide;
N-(6-methylpyridin-2-yl)-2,6-dichloroisonicotinic acid amide;
N-(4-methylpyridin-2-yl)-2,6-dichloroisonicotinic acid amide;
N-(5-chloropyridin-2-yl)-2,6-dichloroisonicotinic acid amide; and
N-pyridin-4-yl-2,6-dichloroisonicotinic acid amide.

5. A composition for protecting plants against attack by microorganisms that contains as active ingredient a microbicidally effective amount of at least one compound of formula I according to claim I together with a suitable carrier therefor.

6. A method of protecting plants against attack by phytopathogenic microorganisms which comprises applying as active ingredient to the plant or the locus thereof a microbicidally effective amount of a compound of formula I according to claim 1.

* * * * *